US010617610B2

(12) United States Patent
Landa et al.

(10) Patent No.: US 10,617,610 B2
(45) Date of Patent: Apr. 14, 2020

(54) UV-PROTECTIVE COMPOSITIONS

(71) Applicant: LANDA LABS (2012) LTD., Rehovot (IL)

(72) Inventors: Benzion Landa, Nes Ziona (IL); Sagi Abramovich, Ra'anana (IL); Snir Dor, Petach Tikva (IL)

(73) Assignee: LANDA LABS (2012) LTD., Rehovot (IL)

( * ) Notice: Subject to any disclaimer, the term of this patent is extended or adjusted under 35 U.S.C. 154(b) by 178 days.

(21) Appl. No.: 15/744,816

(22) PCT Filed: Jul. 22, 2016

(86) PCT No.: PCT/IB2016/054397
§ 371 (c)(1),
(2) Date: Jan. 14, 2018

(87) PCT Pub. No.: WO2017/013633
PCT Pub. Date: Jan. 26, 2017

(65) Prior Publication Data
US 2018/0263864 A1    Sep. 20, 2018

(30) Foreign Application Priority Data

| May 5, 2015 | (GB) | 1607831.3 |
| Jul. 22, 2015 | (GB) | 1512958.8 |
| Apr. 6, 2016 | (GB) | 1605857.0 |

(51) Int. Cl.
| *A61K 8/02* | (2006.01) |
| *A61K 8/29* | (2006.01) |
| *A61K 8/81* | (2006.01) |
| *A61Q 17/04* | (2006.01) |
| *A61K 8/19* | (2006.01) |

(52) U.S. Cl.
CPC .......... *A61K 8/0254* (2013.01); *A61K 8/0241* (2013.01); *A61K 8/0283* (2013.01); *A61K 8/19* (2013.01); *A61K 8/29* (2013.01); *A61K 8/8135* (2013.01); *A61K 8/8147* (2013.01); *A61Q 17/04* (2013.01); *A61K 2800/412* (2013.01); *A61K 2800/413* (2013.01); *A61K 2800/546* (2013.01)

(58) Field of Classification Search
CPC ........ A61K 2800/412; A61K 2800/413; A61K 2800/546; A61K 8/0241; A61K 8/0254; A61K 8/0283; A61K 8/19; A61K 8/29; A61K 8/8135; A61K 8/8147; A61Q 17/04
See application file for complete search history.

(56) References Cited

U.S. PATENT DOCUMENTS

| 6,361,782 B1 | 3/2002 | Chevalier et al. |
| 2004/0137028 A1 | 7/2004 | de la Poterie |
| 2013/0264523 A1* | 10/2013 | Rathschlag ........... C09C 1/0081 |
| | | 252/502 |
| 2016/0324742 A1 | 11/2016 | Sueda et al. |

FOREIGN PATENT DOCUMENTS

| CN | 1804152 | 7/2006 | |
| CN | 1884095 | 12/2006 | |
| CN | 102583519 | 7/2012 | |
| CN | 102963925 | 3/2013 | |
| CN | 102963929 | 3/2013 | |
| EP | 497144 | 5/1992 | |
| EP | 2229931 | * 9/2010 | .............. A61K 8/04 |
| GB | 2431103 | 1/2007 | |
| JP | H1112129 | 1/1999 | |
| JP | H11166173 | 6/1999 | |
| WO | 2013/020261 | 2/2013 | |
| WO | 2015/098992 | 7/2015 | |
| WO | 2016/151537 | 3/2016 | |

OTHER PUBLICATIONS

Bull. Korean Chem. Soc. 2009, vol. 30, No. 12 3021-3024, Dec. 2009, Jum Suk Jang et al., "Energy Band Structure and Photocatalytic Property of Fe-doped Zn 2 TiO 4 Material".
J Sol-Gel Sci Technol 53:135-140, Sep. 2009, Hua Ke et al, "Crystallization process of lanthanum-substituted bismuth titanate synthesized by a facile sol-gel method".
Journal of Nanoscience and Nanotechnology, vol. 15, pp. 8195-8198, Oct. 2015, Myoung Geur Song et al, "The effect of annealing temperature on the bandgap of Bi3.25La0.75FeTi2O12 powders".
Materials Science and Engineering B, vol. 178, pp. 520-526, May 2013, Xue Lin et al, "Photocatalytic degradation of azo dye using Bi3.25M0.75Ti3O12 nanowires . . . ".
Nano convergence vol. 2 No. 1, Apr. 2015, Jun Young Han, "Influence of transition metal doping (X=Co, Fe) on structural, optical properties of Ferroelectric Bi3.25La0.75X1Ti2O12".
CN 1804152—machine translation.
CN 1884095—machine translation.
CN 102583519—machine translation.
CN 102963925—machine translation.
CN 102963929—machine translation.
JP H1112129—machine translation.
JP H11166173—machine translation.

* cited by examiner

*Primary Examiner* — Anna R Falkowitz
(74) *Attorney, Agent, or Firm* — Marc Van Dyke

(57) ABSTRACT

Disclosed are UV-protective compositions comprising swelled polymer matrix macroparticles comprising a thermoplastic polymer swelled with at least one swelling agent, and a plurality of nanoparticles of an inorganic UV-protective agent comprising at least one solid inorganic crystal and a dispersant associated with the crystal, wherein the inorganic nanoparticles are dispersed and embedded in the swelled polymer matrix macroparticles. Method of preparation and uses of such compositions are also provided.

19 Claims, 7 Drawing Sheets

UV-PROTECTIVE COMPOSITIONS

FIELD

The disclosure relates to the field of protection from ultraviolet radiation, and more particularly, to UV-protective compositions comprising nanoparticles of a UV-protective agent consisting of solid inorganic crystals dispersed and embedded in a polymer matrix in the form of macroparticles, to methods for preparing the same and uses thereof.

BACKGROUND

Ultraviolet (UV) radiation is ubiquitous, the sun being the most common source of UV radiation although not the only source. As UV radiation can cause damage to people, animals and objects, compositions that provide protection from UV radiation are useful.

In the biological context, UV-protective compositions, i.e. compositions that reduce or block the transmission of UV rays, are commonly employed to protect against sunburn. Sunburn is a form of radiation burn resulting from an overexposure to ultraviolet (UV) radiation typically from the sun, but also from artificial sources, such as tanning lamps, welding arcs, and ultraviolet germicidal irradiation.

Normal symptoms of sunburn in humans and other animals include reddening of the skin, general fatigue and mild dizziness. An excess of UV radiation can be life-threatening in extreme cases. Excessive UV radiation is considered to be the leading cause of non-malignant skin tumors, as well as increasing the risk of certain types of skin cancer.

Sunscreen compositions are commonly used to prevent sunburn and are believed to prevent squamous cell carcinomas and melanomas. Furthermore, they have been reported to delay the development of wrinkles and additional age-related skin conditions.

Specifically, sunscreen compositions are topical compositions that include UV-protecting agents that absorb and/or reflect at least some of the sun's UV radiation on areas of skin exposed to sunlight, and thus reduce the effect of UV radiation on the skin. Depending on their mode of action, they are typically classified as chemical or physical sunscreens.

Chemical sunscreen compositions comprise organic compounds that absorb UV radiation to reduce the amount of UV radiation that reaches the skin. Being transparent to visible light and thereby being invisible when applied to the skin, chemical sunscreen compositions are popular for use. However, some organic compounds used in chemical sunscreen compositions have been found to generate free radicals which can cause skin damage, irritation and accelerated aging of the skin. Furthermore, organic materials may be absorbed into the skin, resulting in long-term detrimental health effects. Chemical sunscreen compositions may require the addition of a photostabilizer.

Physical sunscreen compositions reflect and absorb UV radiation. Known physical sunscreen compositions comprise particles of inorganic materials, mainly titanium oxide and/or zinc oxide. In order to obtain absorption and/or reflection of ultraviolet radiation over the full UVA and UVB range, relatively large particles are used. Due to the large particle size, such sunscreen compositions are viscous and opaque and tend to leave a white cast on the skin.

Many sunscreen compositions protect against UV radiation in the 280-315 nanometer (nm) range (UVB radiation) that causes sunburn, but do not against UV radiation in the 315-400 nm range (UVA radiation), which does not primarily cause sunburn but can increase the rate of melanoma and photodermatitis.

It is generally preferred that sunscreen compositions are transparent on the skin. In order for physical sunscreen compositions to be transparent, the particles of inorganic material should be in the form of nanoparticles, which absorb and/or scatter UV light but not visible light, rendering them substantially transparent on the skin. However, use of nanoparticles reduces the range of wavelengths absorbed by the inorganic materials. Some known sunscreen compositions therefore block both UVA and UVB radiation by use of a combination of different UV-absorbing or scattering materials, generally termed UV-protecting agents, each of which blocks radiation over a limited range of the UV spectrum.

Similarly, UV-protective compositions can benefit inert materials or objects that may be negatively affected by UV radiation. For instance, UV radiation can reduce the life-span of materials (e.g., natural and synthetic polymers), and may modify colors of objects, especially in articles that are subjected to prolonged sun exposure, such as buildings or vehicles.

Various coatings are known to provide protection against UV radiation damage by blocking or reducing transmission of UV rays. Use of such coatings may in turn reduce the detrimental effect of UV radiation on a living animal. For example, use of said coating on optical lenses, thereby reducing the transmission of UV radiation, may reduce the incidence of UV-induced optical disorders such as cataract. Materials serving for the fabrication of windows incorporating or coated with suitable UV-protecting agents may reduce the transmission of UV radiation to subjects, plants, surfaces or objects shielded by such windows.

International patent application PCT/IB2016/051701, filed on Mar. 24, 2016; GB 1605857.0, filed on Apr. 6, 2016; and GB 1607831.3, filed on May 5, 2016, to the present applicant disclose UV protective compositions comprising inorganic nanoparticles. However, there has been some regulatory concern regarding the safety of such nanoparticles when applied to human skin, based on the public perception of the potential risks posed by particles in the nanometric range.

It would be desirable to have a safe and effective UV protective composition, in particular providing broad-spectrum protection.

SUMMARY

The present disclosure, in at least some embodiments thereof, provides safe and effective ultraviolet radiation (UV)-protective compositions, such as sunscreen compositions, that when applied to a surface provide protection from UV radiation, which in some embodiments have a broad spectrum UV protective activity.

Though in the following, the compositions are generally described for use in living subjects, it is not intended to be limiting, as such compositions may be equally applicable to inanimate objects (e.g., UV protective coating of articles routinely exposed to UV radiation).

According to an aspect of some embodiments, the present disclosure relates to UV-protective compositions, and more particularly, to a UV-protective composition comprising swelled polymer matrix macroparticles comprising a thermoplastic polymer swelled with at least one swelling agent and a plurality of nanoparticles, including inorganic nanoparticles of a UV-protective agent, each of the inorganic nanoparticle comprising at least one doped or undoped solid inorganic crystal and a dispersant associated with the crystal, wherein the inorganic nanoparticles are dispersed and embedded in the matrix macroparticles.

The macroparticles of swelled polymer matrix can be hereinafter simply referred to the matrix macroparticles or the matrix elements, each such discrete macroparticle or element being of any suitable shape. Matrix macroparticles or matrix elements made of swelled thermoplastic polymer and having relatively flat platelet-like or flake-like shapes can also be referred to as matrix flakes.

In some embodiments, the inorganic nanoparticles of at least one inorganic UV-protective agent are dispersed and embedded in swelled polymer matrix flakes; wherein each flake of the swelled polymer matrix flakes has a flake length (Lf), a flake width (Wf), and a flake thickness (Tf), the swelled polymer matrix flakes having a dimensionless flake aspect ratio (Rf) defined by:

$$Rf=(Lf \cdot Wf)/(Tf)^2$$

wherein, with respect to a representative group of the swelled polymer matrix flakes, an average Rf is at least 5;

wherein said plurality of nanoparticles within the representative group has an average particle size ($D_N 50$) of at most 100 nm;

and wherein the inorganic UV protective-agent exhibits at least one, and typically two or three of the following hardness properties:

a Knoop Hardness Number (KHN) within a range of 140 to 1600;

a Vickers Hardness Number ($VHN_{100}$) within a range of 130 to 1500;

a Mohs Hardness Number within a range of 3.5 to 8.

In some embodiments, the dimensions of the various particles (nanoparticles, macroparticles, flakes, etc.) may be estimated by scanning electron microscope (SEM), transmission electron microscope (TEM) focused ion beam (FIB), and/or by confocal laser scanning microscopy techniques. For instance, scanning electron microscopy may be used for assessment of the planar dimensions, while thickness or length of particles can be determined by focused ion beam FIB technique.

While selecting a representative particle, or a group of representative particles, which may accurately characterize various properties of the particle population, it will be appreciated that a more statistical approach may yet more accurately characterize such properties. Thus, in some embodiments of the present disclosure, various dimensional properties, including the dimensionless aspect ratio of the particles, may be determined by analysing, in its entirety, a representative field of view of the relevant image-capturing instrument(s) (e.g., SEM-FIB). Such field of view may also be referred to as an "instrumental filed of view". Typically, the magnification of any appropriate instrument (e.g., microscope, DLS) is adjusted such that at least 10 particles, at least 20 particles, or at least 50 particles are disposed within a single instrumental field of view. By way of example, the dimensionless flake aspect ratio for a group of particles may be volume-averaged, surface-area averaged, or number averaged.

As used herein in the specification and in the claims section that follows, the term "particle length", "flake length", or "Lf", is used generally (and particularly within the context of a "dimensionless flake aspect ratio"), to refer to a maximum length of a particle in its long direction. Perpendicular to Lf (and the like) is measured the "particle width", "flake width", or "Wf". Lf, Wf and the like may be quantitatively evaluated from a field of view image (e.g., from a "footprint" of the flake or particle) of a suitable image-capturing instrument, such as SEM-FIB.

As used herein in the specification and in the claims section that follows, the term "flake thickness", or "(Tf)", at least within the context of a "dimensionless flake aspect ratio", or "(Rf)", refers to a maximum thickness of a particle in its narrow direction, and orthogonal to both respective lines defining the particle length, or flake length (Lf), and the particle width, or flake width (Wf), typically as viewed in a field of view of a suitable image-capturing instrument, such as SEM-FIB.

As used herein in the specification and in the claims section that follows, the term "long dimension" refers to the maximum long dimension of a particle (such as a polymer flake or an inorganic nanoparticle) as viewed in a field of view of an image-capturing instrument, such as SEM-FIB.

In some embodiments, the inorganic nanoparticles of the at least one inorganic UV protective-agent make up at least 20%, at least 35%, at least 50%, at least 65%, at least 80%, at least 90%, or substantially all of the total amount of nanoparticles, by weight, by volume, by cross-sectional area, and/or by number, as may be determined by various instrumental (such as chemical and/or physical) and computational techniques known to those of skill in the art.

A thermoplastic polymer is said to be "swellable" if it can absorb and retain a swelling liquid resulting in weight gain and/or a volume gain relative to its own mass or volume in its native form. The degree of swelling indicates the density between polymer chains, softer "low-density" polymers generally having a higher absorbent capacity, allowing them to swell to a larger degree, than harder "high-density" polymers.

Though a variety of swellable polymers may satisfactorily swell in presence of an oil so as to enable the incorporation of solid particles or nanoparticles (e.g., of a UV-protective agent), a thermoplastic polymer showing a weight gain and/or a volume gain of at least 20% when immersed in an oil for a period of up to 4 days, at a temperature of about 50° C. is deemed suitably "swellable" by the oil. Swelling of the swellable polymer with the oil can however be performed under a variety of swelling conditions, elevated temperatures (i.e. above 50° C., e.g., at 60° C. or more, at 75° C. or more, or even at 90° C. or more) typically accelerating the swelling process. Homogeneous mixing of the swelling polymer within the swelling liquid can also shorten the swelling period.

While swellable polymers as above-described can be preferred for the preparation of matrix macroparticles, the thermoplastic polymer needs not necessarily be swelled to its greatest possible extent to be used according to the present teachings. As used herein, the term "swelled" with regard to a polymer refers to a polymer, also termed a swollen polymer matrix, which shows a weight gain of at least 10% under elected swelling conditions, as compared to the polymer weight prior to said swelling. It is believed that the degree of actual swelling may facilitate the size-reduction of the polymer matrix into matrix elements. For this purpose, the thermoplastic polymer needs to be sufficiently swollen (i.e. soften) to permit kneading of the polymer into individual elements, but not too soft so that the resulting elements would loose shape (e.g., flow and merge into neighbouring elements). Proper swelling may also facilitate the later penetration of added particles and their dispersion during the co-milling with the swollen matrix, while ensuring the relative immobilization of the solid nanoparticles of UV-protective agent within the swollen matrix elements, the amount of oil actually absorbed and/or retained during this process possibly additionally depending upon the manufacturing conditions.

The "suitable softening"/swelling of a polymer may depend upon the manufacturing conditions. In some preferred embodiments, the thermoplastic polymer has a softening point or a melting point of not less than 60° C., such that the composition does not excessively soften when applied to a surface at a temperature range in which the composition would normally be used (e.g., would not melt at body temperature of about 37° C. if applied to a human subject). If a combination of polymers is used and/or if the mixture of polymer(s) and swelling agent(s) (hereinafter the "swelling mixture") comprises or further comprises rheological modifiers (e.g., a plasticizer) that may impact such softening property of the resulting matrix elements, then additionally and alternatively, such mixtures of polymers and/or modifiers should preferably display a combined softening point of not less than 50° C. for the swelling mixture.

It is to be noted in this context that some oils may act as partial plasticizers with respect to some polymers. In such a case, a first oil serving to swell the polymer, which may decrease the combined softening point of the swelling mixture to less than 50° C., can still be used for the milling of the swollen polymer with the nanoparticles under temperature conditions below the combined softening temperature. In some embodiments, the inorganic nanoparticles can be added to the swollen polymer matrix while being dispersed in a second oil, the second oil decreasing the softening point of the milling mixture (or further decreasing it in the event the first oil displayed a plasticizing effect). However, once the matrix macroparticles are obtained, this first oil or second oil can be at least partially replaced by a third oil, the third oil not lowering the softening point of the polymer below the optionally desired threshold of 50° C. In some embodiments, the third oil cannot swell the polymer matrix elements, serving only as carrier to such macroparticles now including the nanoparticles of UV-protective agent, optionally within residual amount of the first oil and second oil, if any.

Polymers having too high a softening point or melting point are believed to be less suitable as they would tend to be non swellable. Typically, suitable thermoplastic polymers have at least one of a softening point and a melting point not exceeding 200° C., or possibly not greater than 150° C.

Advantageously, the dispersed nanoparticles of UV-protective agent do not substantially migrate out of the swelled polymer matrix macroparticles. In such case, the nanoparticles of UV-protective agent may also be said to be embedded in the matrix. Such a situation can be readily ascertained by the lack of nanoparticles in the carrier of the macroparticles, as can be measured or determined by routine methods.

In some embodiments, the solid inorganic crystal of the UV-protective agent is doped. In some embodiments, the solid inorganic crystal is undoped. Crystals may assume any suitable structure providing for the sought UV-protective ability. For instance, titanium dioxide can be of rutile or anatase type, even if their respective activity may differ.

In some embodiments, the inorganic UV protective-agent exhibits at least one, and typically two or three of the following hardness properties:

a) a Knoop Hardness Number (KHN) within a range of 140 to 1600;

b) a Vickers Hardness Number ($VHN_{100}$) within a range of 130 to 1500; and c) a Mohs Hardness Number within a range of 3.5 to 8.

Typically, the KHN is at least 150, at least 160, at least 175, at least 200, or at least 250, and in some cases, at least 350, at least 425, at least 500, or at least 600. The KHN may be at most 1500, at most 1250, at most 1000, or at most 800. In some embodiments, the solid inorganic UV-protective agent has a Knoop Hardness Number between about 300 and about 1000.

Typically, the $VHN_{100}$ is at least 140, at least 150, at least 160, at least 175, at least 200, or at least 250, and in some cases, at least 350, at least 425, at least 500, or at least 600. The $VHN_{100}$ may be at most 1400, at most 1250, at most 1000, or at most 800.

Typically, the Mohs Hardness Number is at least 3.75, at least 4, at least 4.5, or at least 5, and in some cases, at least 5.5 at least 6, or at least 6.5. The Mohs Hardness Number may be at most 7.5 or at most 7.

In some embodiments, the UV-protective agent is selected from the group consisting of a UVA-protective agent and a UVB-protective agent. In some embodiments, the UV-protective agent combines UVA and UVB protective activity.

In some embodiments, the solid inorganic crystal is selected from the group consisting of crystals of doped and undoped metal oxides including, barium compounds, bismuth compounds, titanium compounds and zinc compounds; the oxide being in the form of a mono-oxide, a di-oxide, a tri-oxide, or a tetra-oxide, the oxide further optionally in the form of an oxo-anion.

In some embodiments, the solid inorganic crystal is selected from the group consisting of crystals of barium titanate ($BaTiO_3$), bismuth oxide ($Bi_2O_3$), bismuth vanadate ($BiVO_4$), bismuth titanate ($Bi_4Ti_3O_{12}$), titanium dioxide ($TiO_2$), zinc oxide (ZnO), and zinc titanate ($ZnTiO_4$) any of which may be doped or undoped.

In some embodiments, the solid inorganic crystal comprises a doped metal oxide, optionally wherein the dopant is a metal cation selected from the group consisting of iron, copper, manganese and lanthanum. In the event that metal cations optionally substitute atoms of the at least one inorganic crystal, the so-called "doped" metal oxide crystal is formed.

In some embodiments, the solid inorganic crystal comprises lanthanum-doped bismuth titanate ($Bi_{(4-x)}La_{(x)}Ti_3O_{12}$, wherein x is between 0.1 and 1.5), which may be further doped, optionally with iron.

In some embodiments, the solid inorganic crystal comprises doped zinc oxide comprising from about 90% or even from 95% to about 99.9% molar percentage zinc oxide and from about 0.1% to about 5% or even 10% molar percentage of manganese or copper.

In some embodiments, at least 50%, or at least 55%, or at least 60%, or at least 65%, or at least 70%, or at least 75%, or at least 80%, or at least 85%, or at least 90%, or at least 95%, or at least 97.5%, or at least 99%, per number, of the inorganic nanoparticles of the UV-protective agent have a long dimension (e.g., a length) of up to about 100 nm, or up to about 90 nm, or up to about 80 nm, or up to about 70 nm, or up to about 60 nm. Such dimension can be assessed, for instance, by image analysis of at least one instrumental field of view obtained by suitable microscopic technique and magnification, the at least one field of view comprising at least 10 nanoparticles, the long dimension being the average of the length of the nanoparticles so analysed.

DLS techniques, in which the thickness, length and width of the nanoparticles can be approximated by the hydrodynamic diameter, may facilitate, when appropriate, the analysis of larger samples of nanoparticles. In some embodiments, at least 50%, or at least 55%, or at least 60%, or at least 65%, or at least 70%, or at least 75%, or at least 80%, or at least 85%, or at least 90%, or at least 95%, or at least 97.5%, or at least 99%, per number, per volume, or per surface area, of the inorganic nanoparticles of the UV-protective agent have a cumulative hydrodynamic diameter of up to about 100 nm, or up to about 90 nm, or up to about 80 nm, or up to about 70 nm, or up to about 60 nm.

The characteristic size or dimension that may be obtained for 50% of the inorganic nanoparticles, per number, be it calculated from the length or the hydrodynamic diameter of the nanoparticles, is termed hereinafter the "average particle size", also denoted $D_N50$.

In some embodiments, the nanoparticles consist of doped or undoped solid inorganic crystals having the same chemical formula.

In some embodiments, the nanoparticles of UV-protective agent are present in the swelled polymer matrix macroparticles at a concentration of from about 0.1 to about 60% weight per weight (w/w or wt. %) of the thermoplastic polymer, or from about 1 to about 40% (w/w), or from about 2 to about 30% (w/w), or from about 4 to about 25% (w/w), optionally at a concentration of about 5% (w/w) or about 10% (w/w) or about 25% (w/w) of the thermoplastic polymer.

As the inorganic crystals of UV-protective agent typically have a density higher than the density of the thermoplastic polymer, the relative proportion of nanoparticles to polymer on a volume per volume (v/v) basis can be accordingly reduced. For reference, the density of the UV-protective agents herein disclosed, which may be further affected by the presence and degree of doping, ranges from about 3 g/cm³ (e.g., ~4.23 g/cm³ for titanium dioxide) to about 10 g/cm3 (e.g., ~9.03 g/cm³ for bismuth titanate), while thermoplastic polymers can have a density of about 1 g/cm³ (e.g., ~0.94 g/cm³ for Nucrel® 699).

In some embodiments, the nanoparticles of UV-protective agent are present in the swelled polymer matrix macroparticles at a concentration of from about 0.01 to about 20% (v/v), or from about 0.1 to about 15% (v/v), or from about 1 to about 10% (v/v) of the polymer, optionally at a concentration of about 4% (v/v) or about 6% (v/v) of the polymer.

In some embodiments, wherein the solid inorganic crystal is a crystal of titanium dioxide, the nanoparticles of UV-protective agent are present in the swelled polymer matrix macroparticles at a concentration of about 5.6% (v/v) of the thermoplastic polymer. In some embodiments, wherein the solid inorganic crystal is a crystal of bismuth vanadate, the nanoparticles of UV-protective agent are present in the swelled polymer matrix macroparticles at a concentration of about 3.9% (v/v) of the thermoplastic polymer.

In some embodiments, the macroparticles of swollen polymer embedding the nanoparticles of the UV-protective agent are present at a concentration of no more than 30% (w/w), or of no more than 20% (w/w), of the total UV-protective composition disclosed herein.

In some embodiments, the nanoparticles of UV-protective agent are present at a concentration of from about 0.01 to about 40% (w/w) of the UV-protective composition, or from about 0.1 to about 30% (w/w), or from about 1 to about 20% (w/w), or from about 1 to about 10% (w/w), of the total UV-protective composition.

In some embodiments, the nanoparticles of UV-protective agent are present at a concentration of from about 0.01 to about 20% (v/v) of the UV-protective composition, or from about 0.01 to about 15% (v/v), or from about 0.1 to about 10% (v/v), or from about 0.5 to about 5% (v/v), of the total UV-protective composition.

In some embodiments, the UV-protective composition disclosed herein is generally devoid and/or generally free of an organic ultraviolet-absorbing agent, the composition optionally containing less than 5 wt. %, less than 4 wt. %, less than 3 wt. %, less than 2 wt. %, less than 1 wt. %, less than 0.5 wt. %, less than 0.1 wt. % or less than 0.05 wt. % organic ultraviolet-absorbing agent(s).

In some embodiments, the doped or undoped solid inorganic crystal constitutes the only ultraviolet-absorbing agent in the UV-protective composition disclosed herein.

In some embodiments, the at least one swelling agent comprises an oil.

In some embodiments, the oil is present in the swelled polymer matrix (and macroparticles thereof) at a concentration of from about 5 to about 50% (w/w) of the thermoplastic polymer, or within a range of 10-35% (w/w), or 10-30% (w/w), or 12-25% (w/w), or 15-25% (w/w), optionally at a concentration of about 30% (w/w) or about 20% (w/w) or about 10% (w/w) of the swelled polymer matrix.

In some embodiments, the oil is present in the swelled polymer matrix (and macroparticles thereof) at a concentration of from about 5 to about 65% (v/v) of the thermoplastic polymer, or within a range of 12-45% (v/v), or 12-40% (v/v), or 16-32% (v/v), or 20-30% (v/v), optionally at a concentration of about 40% (v/v) or about 25% (v/v) or about 15% (w/w) of the swelled polymer matrix.

In some embodiments, the oil is selected from the group consisting of mineral oil, natural oil, vegetal oil, synthetic oil, and combinations thereof. Any combinations of oils can be suitable as long as they form a homogeneous fully miscible mixture, compatible with the use envisaged (from polymer swelling to application to target surface, through the incorporation of the nanoparticles and the milling forming the swelled polymer matrix macroparticles).

In some embodiments, the thermoplastic polymer is an oil-swellable thermoplastic homo- or co-polymer, optionally clear, transparent and/or colorless.

In some preferred embodiments, the thermoplastic polymers are functionalized polymers comprising particle-affinic functional group and non-affinic monomer units. For instance, the functional groups may be acidic monomers, whereas the non-affinic groups can be ethylene. In some embodiments, the thermoplastic polymer comprises at least one ethylene polymer, ethylene-acrylic acid (EAA) polymer, ethylene-methacrylic acid (EMMA) polymer, ethyl vinyl acetate (EVA) polymer, substituted or modified versions thereof, ionomers thereof and combinations thereof.

In some embodiments, the thermoplastic polymer comprises at least one ethylene-acrylic polymer, optionally wherein the ethylene-acrylic polymer comprises from about 5 to about 30% (w/w) acrylic monomer. In some embodiments, the ethylene-acrylic polymer is selected from the group consisting of ethylene-methacrylic acid copolymer and ethylene-acrylic acid copolymer.

In some embodiments, at least 50% of the number of swelled polymer matrix macroparticles have a long dimension (e.g., a flake length Lf, characteristic of the planar size of a flake) of up to about 50 micrometer (μm), or of no more than 25 μm, or of no more than 10 μm, or of no more than 5 μm; and/or a width (e.g., a flake width Wf) of no more than 50 μm, or of no more than 25 μm, or of no more than 10 μm, or of no more than 5 μm; and/or a thickness (e.g., a flake thickness Tf) of no more than 1 μm, or of no more than 500 nm, or of no more than 250 nm.

Though swelled polymer matrix macroparticles can assume a variety of shapes, it is believed that relatively flat shapes (e.g., flake-like, platelet-like, having generally regular or irregular contours, etc.) should be preferred. Such shapes are generally characterized by their aspect ratio, the proportional relationship between a characteristic size of the planar dimension (e.g., the longest length of a flake or the average between the longest length and the widest width of the plane) and a characteristic size of their height (e.g., the average thickness of the flake). Generally, geometrical shapes can be considered relatively flat if their aspect ratio is of at least 3:1, or at least 5:1, or at least 10:1, or at least 20:1, or even at least 50:1.

In some embodiments, the swelled polymer matrix macroparticles comprise swelled polymer matrix flakes, the matrix flakes having a characteristic planar size (or an average size for a population of matrix macroparticles) of at most 50 µm, at most 25 µm, at most 10 µm or at most 5 µm and having a characteristic thickness (or average thickness) of at most 1 µm, at most 900 nm, at most 750 nm, at most 650 nm, at most 600 nm, at most 550 nm, at most 500 nm, at most 450 nm, at most 400 nm, at most 350 nm, at most 300 nm, or at most 250 nm.

In some embodiments, the matrix flakes have an irregular contour, including for instance relatively narrow appendices, such as tentacles, extending or protruding from a relatively broad body. Such matrix flakes can also be referred to as "tentacular flakes", which will be further described below in reference with FIG. 10.

In some embodiments, the composition further comprises silver particles, optionally silver nanoparticles having a long dimension of up to about 50 nm. In some embodiments, the silver nanoparticles are dispersed and embedded in the matrix elements.

In some embodiments, at least 50%, at least 55%, at least 60%, at least 65%, at least 70%, at least 75%, at least 80%, at least 85%, at least 90%, at least 95%, at least 97.5% or even at least 99% of the number and/or of the volume of the silver nanoparticles present in the composition has a long dimension or a cumulative hydrodynamic diameter of up to about 50 nm.

In some embodiments, wherein the composition comprises silver nanoparticles, the composition is devoid of an additional ultraviolet-absorbing agent.

In some embodiments, the silver particles are present in the composition, if at all, at a concentration in the range of from about 0.01% to about 10% (w/w) of the total composition.

In some embodiments, the composition further comprises one or more of a carrier, an excipient, an additive, and combinations thereof, each said compound being chemically compatible with the polymer, the UV-protective agent, the dispersant, and the oil being used. Carriers, excipients and additives that are cosmetically, dermatologically or pharmaceutically acceptable are preferred for use in living subjects, but such regulatory approvals may not be required for use on the surfaces of inanimate objects. Though such excipients or additives are typically added to the composition following the preparation of the matrix elements comprising the inorganic UV-protective agent, and their optional transfer to a carrier, this is not essential. Any such compound can be incorporated in any of the liquids or mixtures involved in the manufacturing process of the matrix elements. In such a case, the compound may need to be additionally compatible with the process and the step at which it may be introduced. For instance, a preserving agent if added during the swelling of the thermoplastic polymer may have a greater heat resistance than a preserving agent added in a carrier due to be stored a lower temperature.

In some embodiments, the at least one swelling agent (e.g., the oil), thermoplastic polymer, carrier, excipient, and additive are cosmetically acceptable.

In some embodiments, the composition is in a form selected from the group consisting of an aerosol, a cream, an emulsion, a gel, a lotion, a mousse, a paste, a liquid coat and a spray.

In some embodiments, the UV-protective composition is formulated as one of the following: (a) a skin-care composition for application to human or non-human animal skin; (b) a hair-care composition for application to human or non-human animal hair; or (c) a coating composition for application to an inanimate surface.

In a further aspect, embodiments of the present disclosure provide use of afore-described swelled polymer matrix macroparticles (optionally flakes or tentacular flakes) comprising a thermoplastic polymer swelled with at least one swelling agent (for instance, an oil), and nanoparticles of a UV-protective agent, each of said nanoparticles comprising at least one doped or undoped solid inorganic crystal and a dispersant associated with the crystal, wherein the nanoparticles are dispersed and embedded in the swelled polymer matrix macroparticles, for the preparation of a composition for protecting a target surface, such as a surface of a living subject and/or an inanimate object, against a harmful effect of UV radiation. The compositions, comprising an efficacious amount of nanoparticles of UV-protective agent can be formulated as suitable for application upon the intended surfaces, such preparations being known to persons skilled in the relevant formulations.

According to a further aspect of some embodiments of the disclosure, there is provided a method of preparing a UV-protective composition according to any of the embodiments disclosed herein, the method comprising (a) combining the thermoplastic polymer with the at least one swelling agent; (b) mixing said combination of thermoplastic polymer and at least one swelling agent to provide a homogeneous paste of polymer matrix wherein the thermoplastic polymer is swelled with the at least one swelling agent; (c) adding the nanoparticles of UV-protective agent to the homogeneous paste, the nanoparticles being dispersed in an oil that may be same or different to the at least one swelling agent of step a), and (d) milling the mixture of nanoparticles and swollen polymer, so as to size reduce the polymer matrix into swelled polymer matrix macroparticles, while incorporating and/or dispersing the nanoparticles of UV-protective agent in the swelled polymer matrix macroparticles.

In some embodiments, the combination of step (a) and/or the homogenous paste of step (b) comprises at least about 65% (w/w) oil and at most about 35% (w/w) thermoplastic polymer.

The amount of swollen polymer that can be milled with stably oil-dispersed nanoparticles of UV-protective agent, according to step (d) may depend upon the milling system being used, more energetic ones generally enabling higher polymer concentrations, and upon the milling conditions (e.g., temperature, type of media mill, type of beads, speed, and the like factors). In some embodiments, the polymer of the homogeneous paste being milled with the nanoparticles according to the milling of step (d) is present at a concentration not exceeding 25% (w/w) of the mixture.

Depending on their chemical and/or physical properties, thermoplastic polymers, which are known to persons skilled in the art and identified as such by their suppliers, can be characterized either by their melting point (also called melting temperature) or by their softening point (also called softening temperature). Such values are typically provided by the suppliers of the polymers and can be determined according to standard procedures, typically using Differential Scanning Calorimetry (DSC).

In some embodiments, the mixing of step (b) is performed while heating the combination to a temperature (optionally termed, a swelling temperature) of from about 0° C. to about 20° C., or from about 0° C. to about 30° C., or from about 0° C. to about 40° C. above the melting point or softening point of the thermoplastic polymer. Alternatively, the optional heating is performed at the softening temperature or above the softening temperature of the combined polymers and/or mixture thereof with the oil(s), or any other agent acting as plasticizer for the thermoplastic polymer(s), such combination constituting or forming a portion of the swelling mixture. The softening temperature of such swelling polymers or swelling mixtures can be assessed by routine experimentation according to methods known to the skilled persons, for instance by DSC.

In some embodiments, the homogenous paste of polymer matrix obtained in step (b) is cooled below the lowest temperature amongst the melting point or softening point of the thermoplastic polymer and/or of the swelling mixture, if different. In some embodiments, the homogenous paste is cooled to room temperature (about 23° C.), or even to lower temperatures under suitable conditions. For example, in order to avoid water condensation when cooling is to below room temperature, argon atmosphere may be used. Generally, the temperature to which the homogenous paste is cooled should be higher than the glass transition temperature of the polymer in order to maintain its structural integrity.

Cooling can optionally be performed during continuous mixing of the homogenous paste of oil-swelled thermoplastic polymer.

In some embodiments, the addition of the nanoparticles of UV-protective agent to the homogeneous paste of step (c) and/or their co-milling according to step (d) is performed while maintaining the mixture at a temperature below the lowest temperature amongst the melting point or softening point of the thermoplastic polymer and/or of swelling mixture, if different.

In some embodiments, the nanoparticles of step (c) are dispersed in an oil, or mixture of oils, (the second oil) that may be the same or different than the at least one swelling agent in which the thermoplastic polymer is being swelled, the swelling agent also being optionally an oil or mixture of oils (the first oil). If different, all said oils or combinations thereof shall form a homogeneous and stable mixture.

In some embodiments, the nanoparticles of step (c) are separately prepared by milling particles of the same solid inorganic crystal in an oil, said milling being in presence of a dispersant. Milling techniques are known, and the skilled person can select milling conditions providing inorganic nanoparticles of desired size (e.g., $D_N 50 \leq 100$ nm).

Such steps are schematically illustrated in FIG. 11, in which steps (a) and (b) are combined into S101, the optional cooling of the swollen polymer matrix is represented by S102, the addition of the inorganic nanoparticles of UV-protective agent to the homogeneous paste of step (c) is represented by S103, their co-milling according to step (d) is represented by S104.

Suitable inorganic nanoparticles of UV-protective agents, if commercially available or prepared in a medium other than an oil, can be transferred to an oil vehicle by any compatible method able to maintain the desired particle size and dispersibility of the nanoparticles. For instance, if provided in an aqueous medium, the medium can be removed by evaporation or the nanoparticles can be freeze-dried or any other such method known to the skilled person, as long as the dried nanoparticles can readily redisperse in a desired oil. Optionally the redispersion of the nanoparticles of UV-protective agent in the oil (or mixture of oils) of interest can be performed following the addition of an oil-compatible dispersant and the performance of a dispersing or size-reducing step decreasing the amount of agglomerates that may form during the change of media.

It is to be noted that the incorporation of coarse inorganic UV-protective agents, instead of the nanoparticles as previously described, and directly co-milling these coarse UV-protective agents with the swollen polymer matrix may yield unsatisfactory results. For instance, since such inorganic UV-protective agents have a relatively high hardness (e.g., a Mohs hardness of at least 3.5 or at least 4), reducing their size to nanoparticles (e.g., having a $D_N 50$ of at most 100 nm, at most 80 nm or at most 60 nm) in the presence of the thermoplastic polymer may disadvantageously affect the matrix elements. Additionally, the aspect ratio of the polymer matrix flakes may be appreciably compromised, and their ability to embed the inorganic nanoparticles may also be reduced.

In some embodiments, the dispersant used for the preparation of oil-dispersed nanoparticles of a UV-protective agent consisting of at least one solid inorganic crystal, whether by direct milling in an oil or by redispersion of nanoparticles supplied or prepared in a medium other than an oil, is an oil-compatible dispersant having an Hydrophilic-Lipophilic Balance (HLB) value of no more than 9, or no more than 6, or even no more than 3.

In some embodiments, the dispersant used for the preparation of oil-dispersed nanoparticles of a UV-protective agent is the sole dispersant of the composition. In some embodiments, no additional dispersant is added to or included in any other step of the method herein disclosed. In particular, when the matrix macroparticles have the shape of tentacular flakes, it is believed that the "tentacles" jutting out of the flakes sterically hinder the encroachment between adjacent flakes, thereby facilitating separation and dispersion of the particles.

In some embodiments, the method further comprises, subsequent to (c) adding the inorganic nanoparticles of UV-protective agent to the homogeneous paste of swollen polymer, the nanoparticles being in an oil identical to or compatible with the swelling agent(s) of the thermoplastic polymer, (d) milling the paste to provide swollen polymer matrix macroparticles (optionally flakes or tentacular flakes) having a long dimension (e.g., a flake length, Lf) of up to about 50 μm. In some embodiments, subsequent to milling according to step (d), at least 50% of the number of swollen polymer matrix macroparticles has at a long dimension or Lf of up to about 50 μm.

In some embodiments, the UV-protective composition is manufactured and formulated as a sunscreen composition for application to skin or hair of a human or non-human living subject. In some embodiments, the composition is manufactured and formulated as a composition for application to a surface of an inanimate object.

According to a further aspect of some embodiments of the disclosure, there is provided a sunscreen composition according to any of the embodiments disclosed herein, for use in protecting a subject against a harmful effect of ultraviolet radiation.

According to one embodiment, there is provided a composition as described herein, for use in protecting the skin of a subject against a harmful effect of ultraviolet radiation. In some such embodiments the composition is in the form of a topical composition. In such embodiments, the composition can be in any form suitable to skin-care products, such as facial-care products, make-up products, body-care products, hand-care products and/or foot-care products. Such skin-care products can be applied to the skin of a subject by any conventional method and/or for any duration of time that need not be detailed herein.

According to a further embodiment, there is provided a composition as described herein, for use in protecting the hair of a subject against ultraviolet radiation.

In some such embodiments, the composition is optionally in the form of a hair-care product selected from the group consisting of a shampoo, a conditioner and a hair mask. Such hair-care products can be applied to the hair of a subject by any conventional method and/or for any duration of time that need not be detailed herein.

In some embodiments of the methods disclosed herein, the subject is a human subject. In alternative embodiments of a use of the composition, the subject is a non-human animal.

In some embodiments of the use of the composition, the target surface is a surface of an inanimate object, such as, for example, an object, or a material. In some such embodiments, the composition is in the form of a coating, including liquid coatings, such as a varnish, a lacquer or an emulsion, and non-liquid coatings, such as a paste, a gel, or a mousse. Though UV-protective compositions applicable to the surfaces of inanimate objects are herein referred to as "coatings", it will be readily understood that such compositions may also permeate, impregnate or be otherwise embedded at least to some extent within the surfaces of the objects being protected. Such coating products can be applied to the surface of an inanimate object by any conventional method that need not be detailed herein.

In some embodiments, protecting against ultraviolet radiation comprises protecting against a harmful effect of ultraviolet A radiation and ultraviolet B radiation.

As used herein, the term "nanoparticles" refers to particles of UV-protective agent of any suitable shape wherein the size of a long dimension is 100 nm or less, 90 nm or less, 80 nm or less, 70 nm or less, or even 60 nm or less.

In some embodiments, the long dimension of the nanoparticles is at least about 10 nm, at least about 15 nm or at least about 20 nm.

In some embodiments, the size of the nanoparticles of UV-protective agent and/or the size of the swelled polymer matrix macroparticles is determined by microscopy techniques, as known in the art. If assessing the respective populations of nanoparticles or macroparticles is desired, such microscopic measurements are repeated on a number of particles. Certain microscopes incorporate image analyser able to readily provide metrics of relevance to the population of particles captured in the relevant field of view. Depending on the microscopy technique, the magnification and the size of the particles under investigation, a field of view may include at least 5 particles, at least 10 particles, or at least 20 particles; and optionally, at most 200 particles, or at most 100 particles, or at most 50 particles.

In some embodiments, the size of the nanoparticles of UV-protective agent, or of the macroparticles of swelled polymer matrix, is determined by Dynamic Light Scattering (DLS). In DLS techniques the particles, whether in the sub-micron "nano range" or above micron "macro range", are approximated to spheres of equivalent behavior and the size can be provided in term of hydrodynamic diameter.

DLS also allows readily assessing the size distribution of a population of particles. Such method, though not exclusive, is preferred to assess if the size distribution of the particles is or not substantially unimodal (i.e. having a single or highly predominant peak).

Distribution results can be expressed in terms of the hydrodynamic diameter for a given percentage of the cumulative particle size distribution, either in terms of numbers of particles (denoted $D_N$) or volumes (denoted $D_V$), and are typically provided for 10%, 50% and 90% of the cumulative particle size distribution. For instance, D50 refers to the maximum hydrodynamic diameter below which 50% of the sample volume or number of particles, as the case may be, exists and is interchangeably termed the median diameter per volume ($D_V50$) or per number ($D_N50$), respectively.

In some embodiments, the nanoparticles of UV-protective agent according to the disclosure have a cumulative particle size distribution of D90 of 150 nm or less, or a D95 of 150 nm or less, or a D97.5 of 150 nm or less or a D99 of 150 nm or less, i.e. 90%, 95%, 97.5% or 99% of the sample volume or number of particles, as applicable, have a hydrodynamic diameter of at most 150 nm, or even of at most 100 nm.

Any hydrodynamic diameter having a cumulative particle size distribution of 90% or 95% or 97.5% or 99% of the nanoparticle population, whether in terms of number of particles or volume of sample, may be referred to hereinafter as the "maximum diameter", i.e. the maximum hydrodynamic diameter of particles present in the population at the respective cumulative size distribution.

It is to be understood that the term "maximum diameter" is not intended to limit the scope of the present teachings to nanoparticles having a perfect spherical shape. This term as used herein encompasses any representative dimension of the nanoparticles at cumulative particle size distribution of at least 90%, e.g. 90%, 95%, 97.5% or 99%, or any other intermediate value, of the distribution of the population.

In some embodiments, the nanoparticles have a unimodal particle size distribution. In alternative embodiments, the nanoparticles have at least a bimodal distribution having a first peak (weight/area) representing a first population of particles and a second peak or subsequent peaks representing a second population or subsequent populations of particles, wherein said first peak is larger than said second peak, and optional subsequent peaks.

According to some embodiments, the nanoparticles have a particle size distribution (volume basis) having a standard deviation of at most 75 nm, at most 60 nm, at most 50 nm, at most 40 nm, at most 35 nm, at most 30 nm, or at most 25 nm.

According to some embodiments, the nanoparticles have a particle size distribution (volume basis) having a standard deviation of at most 100%, at most 80%, at most 60%, at most 50%, at most 40%, or at most 30%.

According to some embodiments, the nanoparticles have a particle size distribution (number basis) having a standard deviation of at most 60 nm, at most 50 nm, at most 40 nm, at most 35 nm, at most 30 nm, at most 25 nm, or at most 20 nm.

According to some embodiments, the nanoparticles have a particle size distribution (number basis) having a standard deviation of at most 80%, at most 60%, at most 50%, at most 40%, at most 30%, at most 25%, or at most 20%.

Though not essential, the nanoparticles may preferably be uniformly shaped and/or within a symmetrical distribution relative to a median value of the population and/or within a relatively narrow size distribution.

A particle size distribution is said to be relatively narrow if at least one of the following conditions applies:
- A) the difference between the hydrodynamic diameter of 90% of the nanoparticles and the hydrodynamic diameter of 10% of the nanoparticles is equal to or less than 150 nm, or equal to or less than 100 nm, or even equal to or less than 50 nm, which can be mathematically expressed by: (D90−D10)≤150 nm and so on; and/or
- B) the ratio between a) the difference between the hydrodynamic diameter of 90% of the nanoparticles and the hydrodynamic diameter of 10% of the nanoparticles; and b) the hydrodynamic diameter of 50% of the nanoparticles, is no more than 2.0, or no more than 1.5, or even no more than 1.0, which can be mathematically expressed by: (D90−D10)/D50≤2.0 and so on; and/or
- C) the polydispersity index of the particles is equal to or less than 0.4, or equal to or less than 0.2, or even equal to or less than of 0.1, which can be mathematically expressed by: PDI=$\sigma^2/d^2$≤0.4 and so on, wherein $\sigma$ is the standard deviation of the nanoparticles distribution and d is the mean size of the nanoparticles.

In some embodiments, the compositions disclosed herein are substantially invisible to the human eye, in particular when applied to a subject.

In some embodiments, the compositions are visible to the human eye when applied to a surface, of a subject or of an object. In some such embodiments, the composition may provide a colour that is beneficial in the preparation of a product in which such colour is desirable, e.g. a make-up product such as a blusher, or a tinted coating for application to a surface of an inanimate object. For example, iron doped zinc titanate particles provide a pale reddish colour which may be desirable in some such make-up products.

As used herein, the terms "ultraviolet-protective agent" or "ultraviolet-protecting agent" refer to agents as used in the art that absorb and/or reflect and/or scatter UV radiation on surfaces exposed to sunlight or any other UV source, so as to reduce the effect of UV radiation on the surface. The surface may be the skin and/or hair of a subject, such as a human subject or a non-human animal. The surface may also be the surface (e.g. an exterior face) of an inanimate object.

In another aspect, embodiments of the present disclosure provide a method for the preparation of afore-described compositions.

In a further aspect, embodiments of the present disclosure provide use of afore-described compositions for the preparation of UV-protective compositions capable of reducing the effect of UV radiation on the surface of living subjects and inanimate objects.

Some known UV-protective compositions block both UVA and UVB radiation by use of a combination of different UV-protecting agents, each of which blocks radiation over a limited range of the UV spectrum.

As used herein, the term "broad-spectrum UV absorption" with regard to an ultraviolet-absorbing agent refers to the situation in which the area under the curve (AUC) formed by the UV-absorption of the agent as a function of wavelength in the range of 280 nm to 400 nm ($AUC_{280-400}$) is at least 75% of the AUC formed by the same agent at the same concentration in the range of 280 nm to 700 nm ($AUC_{280-700}$). Similarly, where noted as such herein, the terms "broader-spectrum UV absorption" and "broadest spectrum UV absorption" with respect to a UV-absorbing agent refer respectively to the situation in which the area under the curve (AUC) formed by the absorption of the agent as a function of wavelength in the range of 280 nm to 400 nm ($AUC_{280-400}$) is at least 85% or 95% of the AUC formed by the same agent at the same concentration in the range of 280 nm to 700 nm ($AUC_{280-700}$).

In some embodiments, the area under the curve (AUC) formed by the UV-absorption of the composition as a function of wavelength in the range of 280 nm to 400 nm ($AUC_{280-400}$) is at least 75%, at least 85% or at least 95% of the AUC formed by the same composition in the range of 280 nm to 700 nm ($AUC_{280-700}$).

As used herein, the term "critical wavelength" is defined as the wavelength at which the area under the absorbance spectrum from 290 nm is 90% of the integral of the absorbance spectrum from 290 nm to 400 nm.

In some embodiments, the composition has a critical wavelength of at least 370 nm, such as 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, or greater than 392 nm.

As used herein, the term "ultraviolet-absorbing agent" refers to an agent providing at least 50% absorption of ultraviolet light in the wavelength range of from 290 nm to 400 nm when present in a composition at up to 50% (w/w) of the total composition.

As used herein, the terms "generally devoid of an organic ultraviolet-absorbing agent", "considerably devoid of an organic ultraviolet-absorbing agent", "significantly devoid of an organic ultraviolet-absorbing agent", "substantially devoid of an organic ultraviolet-absorbing agent", "essentially devoid of an organic ultraviolet-absorbing agent", "substantively devoid of an organic ultraviolet-absorbing agent" and "devoid of an organic ultraviolet-absorbing agent" refer respectively to a composition in which a UV-absorbing organic material, if any, is present in the composition at a concentration which provides absorption of not more than 20%, not more than 15%, not more than 10%, not more than 5%, not more than 2%, not more than 1% or not more than 0.5% of ultraviolet light in the wavelength range of from 290 nm to 400 nm.

As used herein, the term "generally devoid of an additional ultraviolet-absorbing agent", "considerably devoid of an additional ultraviolet-absorbing agent", "significantly devoid of an additional ultraviolet-absorbing agent", "substantially devoid of an additional ultraviolet-absorbing agent", "essentially devoid of an additional ultraviolet-absorbing agent", "substantively devoid of an additional ultraviolet-absorbing agent" and "devoid of an additional ultraviolet-absorbing agent" refer respectively to a composition which is devoid of any UV-absorbing material other than that specifically disclosed as being present in the composition at a concentration, which, if included in the composition, provides absorption of not more than 20%, not more than 15%, not more than 10%, not more than 5%, not more than 2%, not more than 1% or not more than 0.5% of ultraviolet light in the wavelength range of from 290 nm to 400 nm.

In some embodiments of the composition, use or method disclosed herein, the composition contains less than 5 wt. % organic UV-absorbing agents. In some embodiments the composition contains less than 4 wt. %, 3 wt. %, 2 wt. % or 1 wt. % organic UV-absorbing agents. In some embodiments the composition is largely free of organic ultraviolet-absorbing agents, i.e. the composition contains less than 0.5 wt. % organic UV-absorbing agents. In some embodiments the composition is mostly free of organic UV-absorbing agents, i.e. the composition contains less than 0.1 wt. % organic UV-absorbing agents. In some embodiments the composition is principally free of organic ultraviolet-absorbing agents, i.e. the composition contains less than 0.05 wt. % organic UV-absorbing agents. In some embodiments the composition is fundamentally free of organic UV-absorbing agents, i.e. the composition contains less than 0.01 wt. % organic UV absorbing agents. In some embodiments of the composition, use or method disclosed herein, the composition is generally devoid of organic ultraviolet-absorbing agents, considerably devoid of organic ultraviolet-absorbing agents, significantly devoid of organic ultraviolet-absorbing agents, substantially devoid of organic ultraviolet-absorbing agents, essentially devoid of organic ultraviolet-absorbing agents, substantively devoid of organic ultraviolet-absorbing agents or devoid of organic ultraviolet-absorbing agents.

In some embodiments of the composition, use or method disclosed herein, the composition contains less than 10 wt. % additional UV-absorbing agents. In some embodiments the composition contains less than 5 wt. %, less than 4 wt. %, less than 3 wt. %, less than 2 wt. % or less than 1 wt. % additional UV-absorbing agents. In some embodiments the composition is largely free of additional ultraviolet-absorbing agents, i.e. the composition contains less than 0.5 wt. % additional UV-absorbing agents. In some embodiments the composition is mostly free of additional UV-absorbing agents, i.e. the composition contains less than 0.1 wt. % additional UV-absorbing agents. In some embodiments the composition is principally free of additional ultraviolet-absorbing agents, i.e. the composition contains less than 0.05 wt. % additional UV-absorbing agents. In some embodiments the composition is fundamentally free of additional UV-absorbing agents, i.e. the composition contains less than 0.01 wt. % additional UV absorbing agents. In some embodiments of the composition, use or method disclosed herein, the composition is generally devoid of additional ultraviolet-absorbing agents, considerably devoid of additional ultraviolet-absorbing agents, significantly devoid of additional ultraviolet-absorbing agents, substantially devoid of additional ultraviolet-absorbing agents, essentially additional of organic ultraviolet-absorbing agents, substantively additional of organic ultraviolet-absorbing agents or devoid of additional ultraviolet-absorbing agents.

In some embodiments of the composition, use or method disclosed herein, the inorganic UV-absorbing agent or mixture of such agents is the sole ultraviolet-absorbing agent in the composition.

Though typically desired for the protection of living subjects, broad-spectrum UV absorption is not necessarily needed for the UV protection of inanimate objects. Some objects may benefit form UV-protecting agents mainly efficient over UVB range.

Aspects and embodiments of the disclosure are described in the specification herein below and in the appended claims.

Unless otherwise defined, all technical and scientific terms used herein have the same meaning as commonly understood by one of ordinary skill in the art to which the disclosure pertains. In case of conflict, the specification, including definitions, will take precedence.

As used herein, the terms "comprising", "including", "having" and grammatical variants thereof are to be taken as specifying the stated features, integers, steps or components, but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise. For instance, a thermoplastic polymer can include a mixture of polymers, an oil can include a mixture of oils, a UV-protective agent can include a mixture of UV-protective agents as herein disclosed and so on.

In the discussion, unless otherwise stated, adjectives such as "substantially" and "about" that modify a condition or relationship characteristic of a feature or features of an embodiment of the present technology, are to be understood to mean that the condition or characteristic is defined within tolerances that are acceptable for operation of the embodiment for an application for which it is intended. In particular, when a numerical value is preceded by the term "about", the term "about" is intended to indicate +/−10%, or +/−5%, or +/−2% of the mentioned value.

Additional objects, features and advantages of the disclosure will be set forth in the detailed description which follows, and in part will be readily apparent to those skilled in the art from the description or recognized by practicing the disclosure as described in the written description and claims hereof, as well as the appended drawings. Various features and sub-combinations of embodiments of the disclosure may be employed without reference to other features and sub-combinations.

It is to be understood that both the foregoing general description and the following detailed description, including the materials, methods and examples, are merely exemplary of the disclosure, and are intended to provide an overview or framework to understanding the nature and character of the disclosure as it is claimed, and are not intended to be necessarily limiting.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

Figure 1:
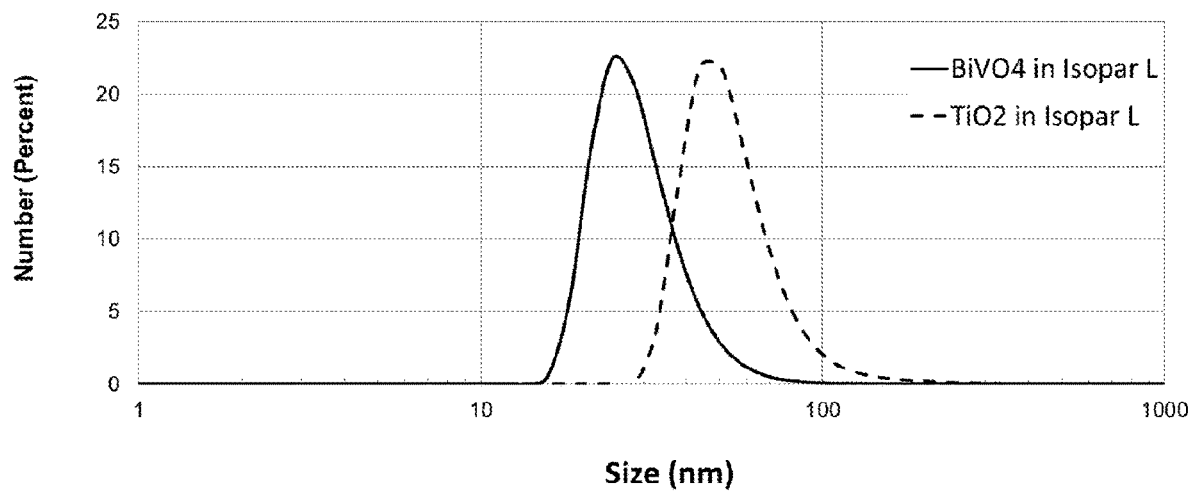
FIG. 1 is a line graph showing Particle Size Distribution (PSD) of bismuth vanadate and titanium dioxide nanoparticles in Isopar™ L after milling, expressed as number percentage.

The present disclosure, in at least some embodiments, provides UV-protective compositions, such as sunscreen compositions for protection against ultraviolet radiation, uses of such compositions and methods of making such compositions.

The UV-protective compositions disclosed herein comprise swelled polymer matrix macroparticles (optionally flakes), comprising a thermoplastic polymer swelled with at least one swelling agent, optionally an oil, and a plurality of nanoparticles including inorganic nanoparticles of at least one UV-protective agent, each of the inorganic nanoparticles comprising at least one solid inorganic crystal and a dispersant associated with the crystal, wherein the inorganic nanoparticles are dispersed and embedded in the swelled polymer matrix macroparticles.

The plurality of nanoparticles, including the inorganic nanoparticles of a UV-protective agent, the inorganic nanoparticles comprising the solid inorganic crystals of the UV-protective agent and the dispersant associated therewith, can be hereinafter simply referred to the inorganic nanoparticles, or the inorganic nanoparticles of UV-protective agent, or the inorganic nanoparticles of inorganic UV-protective agent, and like modification, unless otherwise clearly dictated by the context. Such inorganic nanoparticles can assume a variety of shapes, such as sphere-like, rod-like or platelet like, as long as the average particle size of such nanoparticles does not exceed 100 nm, as detailed herein.

As used herein, the term "dispersed" indicates that the nanoparticles of UV-protective agent are "well dispersed" and/or "uniformly distributed" within the swelled polymer matrix macroparticles. "Well dispersed" nanoparticles are individual particles expected to have an absorbance highly similar to the absorbance of same particles when oil-dispersed prior to their incorporation into the matrix elements, a similar spectrum ruling out the undesired formation of agglomerates of nanoparticles within the swollen polymer. "Uniformly distributed" nanoparticles are expected to be present in similar numbers in cells of view of same size, the cells being subdivisions of a microscopic field of view capturing a representative portion of the matrix macroparticle. Depending on the magnification, a field of view can be divided in a different number of non-overlapping cells of same area. The particles are counted in at least three such cells and the number of particles in each cell should not vary by more than 30% amongst the different cells, such measurements being preferably performed on cells of view of similar thicknesses. In this context it should be noted that some microscopic analysis suggest the presence of clusters of particles, which may however represent individual particles residing at different depths within a given matrix macroparticle.

As used herein, the term "embedded" indicates that the nanoparticles of UV-protective agent are fixedly incorporated within the swelled polymer matrix macroparticles. The term "embedded" is used to exclude situations in which UV-protective agents would essentially exclusively coat or be otherwise externally associated with a polymer core.

It has surprisingly been found by the present applicant that, although reduction of particle size of known inorganic UV-absorbing agents to nanometric dimensions (e.g., below 1 micrometer (µm), typically below 100 nm) is known to significantly reduce the maximum wavelength of light, including UV light, which is effectively absorbed by the particles, UV protective compositions according to the present teachings comprising doped or undoped crystals of solid inorganic material milled to nanoparticle size still provide substantial absorption of UV radiation of wavelength from 280 nm (or even shorter wavelength) up to about 400 nm, thus providing broad-spectrum protection against both UVA and UVB radiation, even in the absence of additional ultraviolet-absorbing agents.

The present applicant previously established that UV-protective compositions comprising doped or undoped solid inorganic material, such as barium titanate, bismuth oxide, bismuth vanadate, bismuth titanate, titanium dioxide, zinc oxide, or zinc titanate, milled to nanoparticle size, still provide substantial absorption of UV radiation of wavelength from at least 280 nm up to at least 400 nm, thus providing broad-spectrum protection against both UVA and UVB radiation, even in the absence of additional ultraviolet-absorbing agents. However, there is some public concern regarding nanoparticles in general and their application, for instance, to the skin or hair of a human subject, which has been considered to possibly be associated with certain harmful effects.

It has surprisingly been found by the present applicant that the compositions described herein provide broad spectrum protection, in some embodiments against both UVA and UBV radiation, while having reduced potential toxicity compared to compositions comprising nanoparticles of a UV-protective agent comprising solid inorganic crystals in the absence of a polymer matrix. In some embodiments, the composition has low visibility when applied to a surface such as the skin or hair of a living subject.

Thus, in some embodiments, UV-protective compositions disclosed herein comprise nanoparticles of a UV-protective agent comprising at least one solid inorganic crystal, such as a crystal of a barium compound (for example, barium titanate), a bismuth compound (for example, bismuth vanadate, bismuth oxide or bismuth titanate), a titanium compound (for example, titanium dioxide), or a zinc compound (for example, zinc oxide or zinc titanate), dispersed and embedded in swelled polymer matrix macroparticles (such as flakes).

In some embodiments, at least 50%, or at least 55%, or at least 60%, or at least 65%, or at least 70%, or at least 75%, or at least 80%, or at least 85%, or at least 90%, or at least 95%, at least 97.5% or even at least 99% of the inorganic nanoparticles of the UV-protective agent, in terms of number or volume of particles, have a long dimension not exceeding 100 nm.

In some embodiments, the inorganic nanoparticles of UV-protective agent have an average particle size ($D_N50$) of up to about 100 nm, 90 nm, 80 nm, 70 nm or even up to 60 nm. In some embodiments, the nanoparticles have a $D_N50$ in the range of from about 10 nm to about 80 nm, from about 10 to about 70 nm, from about 20 to about 70 nm or from about 20 to about 60 nm. In some embodiments, the average particle size of the inorganic nanoparticles is the average of the length of 50% of the particles, by number. In some embodiments, the average particle size of the inorganic nanoparticles is the cumulative hydrodynamic diameter of 50% of the particles, by number.

In some embodiments, the afore-mentioned characteristic sizes or ranges of sizes, be them derived from the length or the hydrodynamic diameter of the inorganic nanoparticles, apply to at least 55%, or at least 60%, or at least 65%, or at least 70%, or at least 75%, or at least 80%, or at least 90%, at least 95%, or at least 97.5% or at least 99% of the number of the inorganic nanoparticles.

In some embodiments, the average particle size of the nanoparticles of UV-protective agent is expressed in terms of the hydrodynamic diameter as measured by DLS techniques. In some embodiments, the population distribution of the nanoparticles is expressed in terms of the cumulative particle size distribution, according to the number of particles in a sample, the hydrodynamic diameter at any given cumulative percentage point of the population being also referred to as the cumulative hydrodynamic diameter.

In some embodiments, the maximum diameter of the nanoparticles (i.e. the hydrodynamic diameter of at least 90% of the population of particles) is assessed for population distribution measured in terms of number of particles and percentage thereof.

In some embodiments, the inorganic nanoparticles of UV-protective agent dispersed and embedded in the swelled polymer matrix macroparticles are not visible to the human eye, in particular when applied to the skin or hair of a subject, due to their lack of absorbance in the visible range.

In some embodiments, the inorganic nanoparticles of UV-protective agent dispersed and embedded in the swelled polymer matrix macroparticles are blended into a coloured composition and need not be substantially transparent and/or invisible, for instance when used in a make-up product, such as a foundation, which is slightly tinted when applied to the skin of a subject or when used in a tinted coating to be applied to an inanimate surface for instance, of similar color.

In some embodiments, the nanoparticles of the inorganic UV-protective agent are present in the swelled polymer matrix macroparticles in a weight per weight concentration of from about 0.1 to about 60% (w/w) of the thermoplastic polymer, such as from about 0.5 to about 50% (w/w), from about 1 to about 40% (w/w), from about 2 to about 30% (w/w) or from about 4 to 25% (w/w). In some embodiments, the inorganic nanoparticles are present in the swelled polymer matrix macroparticles at a concentration of about 5% (w/w), about 10% (w/w), about 20% (w/w) or of about 25% (w/w) of the thermoplastic polymer.

In some embodiments, the nanoparticles of the inorganic UV-protective agent are present at a concentration of up to about 40% (w/w) of the total composition, such as up to about 30%, up to about 25%, up to about 20% or even up to about 10% (w/w) of the total UV-protective composition.

In some embodiments, the nanoparticles of the inorganic UV-protective agent are present in the composition at a concentration of from about 0.01% (w/w) to about 40% (w/w), from about 0.1% (w/w) to about 30% (w/w), from about 1% (w/w) to about 20% (w/w), or even from about 1% (w/w) to about 10% (w/w) of the final UV-protective composition. In some embodiments, the inorganic nanoparticles of UV-protective agent are present at a concentration of about 4% (w/w) of the final composition.

Suitable thermoplastic polymers are swellable (optionally, oil-swellable) thermoplastic homopolymers or copolymers, preferably clear, transparent and/or colorless. The thermoplastic polymers are preferably functionalized polymers comprising particle-affinic functional group and non-affinic monomer units. The monomer units bearing the particle-affinic functional groups and the non-particle-affinic monomer units can be assembled as a copolymer, including a random copolymer, a block copolymer, an alternating copolymer or a grafted copolymer, and wherein said copolymer can be linear, branched, or grafted.

For instance, the functional groups may be acidic monomers, whereas the non-affinic groups can be ethylene. In some embodiments, the thermoplastic polymer comprises at least one ethylene polymer, ethylene-acrylic acid (EAA) polymer, ethylene-methacrylic acid (EMMA) polymer, ethyl vinyl acetate (EVA) polymer, substituted or modified versions thereof, ionomers thereof and combinations thereof. In some embodiments, the ionomer is selected from magnesium, sodium and zinc. In some embodiments, the ethylene-acrylic polymer comprises from about 5 to about 30% (w/w) acrylic monomer.

In some embodiments, the thermoplastic polymer is at least one polymer selected from the group consisting of acid modified ethylene acrylate resins, maleic anhydride modified ethylene copolymer, anhydride modified ethylene vinyl acetate, acid/acrylate-modified ethylene vinyl acetate, anhydride-modified ethylene/methyl acrylate copolymers, ethylene-vinyl acetate copolymer, copolymer of ethylene and acrylic acid (and zinc ionomers thereof), copolymer of ethylene and methacrylic acid (and zinc ionomers thereof), low density polyethylene (optionally anhydride modified), terpolymer of ethylene, acrylic ester and maleic anhydride, and terpolymer of ethylene-methyl acrylate-maleic anhydride.

Such polymers are commercially available, for example, as Bynel® 2022, Bynel® 4157, Bynel® CXA 2002, Bynel® CXA E214, Bynel® CXA 3036, Bynel® CXA 3048, Bynel® CXA 3095, Bynel® CXA 3101, Bynel® CXA 4109, Bynel® CXA 41E687, Bynel® CXA E-326, Bynel® CXA E-369, Bynel® CXA E-374, Elvax® 460, Elvax® 550, Elvax® 650, Elvax® 660, Elvax® 760, Elvax® 770, Nucrel® 0407, Nucrel® 0609, Nucrel® 699, Nucrel® 0903, Nucrel® 0908, Nucrel® 0910, Nucrel® 925, Nucrel® 1202, Nucrel® 2940, Nucrel® 30707, Nucrel® 31001, Surlyn® 1554, Surlyn® 1652, Surlyn® 1702, Surlyn® 1801, and Surlyn® 9910, available from E.I. du Pont de Nemours and Company, Wilmington, Del., USA.; and as Lotader® 2308, Lotader® 2400, Lotader® 3200, Lotader® 3210, Lotader® 3300, Lotader® 3410, Lotader® 6200, Lotader® 8200, and Lotader® TX 8030, available from Arkema, France.

In some embodiments, the at least one swelling agent comprises an oil.

Oils are generally defined as substances substantially water immiscible at room temperature (circa 23° C.) and atmospheric pressure, and typically, but not necessarily, liquid. They can be characterized, among other things, by the source of the oil, the degree of saturation/unsaturation, the type of fatty acids and/or their relative content, the length of carbon chains, and the like typical parameters. The afore-mentioned chemical characteristics may affect physical behaviour, for instance the melting point and/or the softening point and/or the viscosity and/or volatility of the oil, or mixture thereof, at temperatures of interest (e.g., to the formulation process during milling or matrix preparation, to the application process, to the intended use, etc.). As mentioned, the oil may additionally affect the melting point and/or the softening point of the thermoplastic polymers or combinations thereof.

In some embodiments, the oil is selected from the group consisting of a mineral oil, a natural oil, a vegetal oil, an essential oil, a synthetic oil, a mineral oil and combinations thereof. In some embodiments, the oil is a cosmetically acceptable oil conventionally used in the preparation of personal care products.

Suitable mineral oils are clear and odorless derivates/distillates of petroleum.

Non-limiting examples of synthetic oils include synthetic isoparaffins (as commercially available, for instance, from Exxon Mobil Chemical as Isopar™ L, Isopar™ M and Isopar™ V) and the reaction products of C12-C15 Alcohol and Benzoic Acid, namely C12-C15 Alkyl Benzoate (as commercially available from Phoenix Chemical as Pelemol® 256), isononlyl isononanoate (as commercially available from ALZO International, Inc.), C12-C15 alkyl ethylhexanoate (as commercially available from Innospec Performance Chemicals).

Non-limiting examples of suitable vegetal oils include argan oil, chokeberry (seed) oil, avocado oil, apricot kernel oil, peach (pits) oil, canola oil, nigella oil, pumpkin seed oil, wild rose (seeds) oil, pomegranate seeds oil, jojoba oil, cocoa butter, wheat sprout oil, coconut oil, safflower oil, corn oil, camelina oil, flax seed oil, macadamia oil, raspberries seeds oil, meadowfoam seeds oil, *passiflora* seeds oil, almond oil, neem oil, moringa oil, *borago* oil, olive oil, peanuts oil, hazelnuts oil, walnut oil, palm oil, *papaya* seeds oil, parsley seeds oil, seabuckthorn oil, castor oil, rice oil, sesame oil, shea butter, sunflower oil, soybean oil, tamanu oil, evening primrose oil, grape seeds oil, cranberry seeds oil.

Non-limiting examples of essential oils include agar oil, ajwain oil, *angelica* root oil, anise oil, asafetida, balsam of Peru, basil oil, bay oil, bergamot oil, black pepper oil, buchu oil, birch oil, camphor, *cannabis* flower essential oil, caraway oil, cardamom seed oil, carrot seed oil, cedarwood oil, chamomile oil, calamus root oil, cinnamon oil, cistus oil, citron oil, citronella oil, clary sage oil, clove leaf oil, coffee oil, coriander oil, costmary oil, costus root oil, cranberry seed oil, cubeb oil, cumin oil, cypress oil, curry leaf oil, davana oil, dill oil, elecampane oil, *eucalyptus* oil, fennel seed oil, fenugreek oil, fir oil, frankincense oil, galangal oil, *galbanum* oil, ginger oil, goldenrod oil, grapefruit oil, henna oil, helichrysum oil, hickory nut oil, horseradish oil, hyssop oil, Idaho tansy oil, jasmine oil, juniper berry oil, *laurus nobilis* oil, lavender oil, ledum oil, lemon oil, lemongrass oil, lime oil, *litsea cubeba* oil, linaloe oil, mandarin oil, marjoram oil, melissa oil, mentha arvenis oil, moringa oil, mountain savory oil, mugwort oil, mustard oil, myrrh oil, myrtle oil, neem oil, neroli oil, nutmeg oil, orange oil, oregano oil, orris oil, palo santo oil, parsley oil, patchouli oil, *perilla* oil, pennyroyal oil, peppermint oil, petitgrain oil, pine oil, ravensara oil, red cedar oil, Roman chamomile oil, rose oil, rosehip oil, rosemary oil, rosewood oil, sage oil, sandalwood oil, *sassafras* oil, savory oil, schisandra oil, spearmint oil, spikenard oil, spruce oil, star anise oil, tangerine oil, tarragon oil, tea tree oil, thyme oil, *tsuga* oil, turmeric oil, valerian oil, vetiver oil, western red cedar oil, wintergreen oil, yarrow oil, ylang-yland oil and zedoary oil.

In some embodiments, the oil is present at a concentration of from about 10% (w/w) to about 50% (w/w) of the matrix, such as, for example, from about 10 to about 40% (w/w) or from about 20 to about 40% (w/w). In some embodiments, the oil is present at a concentration of about 30% (w/w) of the matrix.

In some embodiments, at least 50% of the swelled polymer matrix macroparticles have a long dimension (e.g., a flake length Lf) of up to about 4 micrometers (μm), up to about up to about 5 μm or up to about 6 μm, up to about 10 μm, up to about 20 μm, up to about 30 μm, up to about 40 μm or even up to about 50 μm. It can be appreciated that the width of a flake not exceeding its length, the width of the flake can be of at most 50 μm, at most 40 μm, at most 30 μm, at most 20 μm, at most 6 μm, or at most 4 μm, as long as Wf≤Lf.

It should be noted that in order for a nanoparticle of UV-protective agent to be successfully dispersed and embedded in a swelled polymer matrix macroparticle, the smallest dimension of the matrix macroparticles (e.g., a flake thickness Tf) should preferably be at least two-fold, four-fold, six-fold, eight-fold or even one order of magnitude greater than the length of the inorganic nanoparticles of UV-protective agent.

The macroparticles of swelled polymer matrix may have any suitable aspect ratio, i.e., a dimensionless ratio between the longest dimension in the largest plane projecting from the particle and a smallest dimension in a direction orthogonal to said plane.

Such dimensions can be assessed on a number of representative macroparticles by methods known in the art, such as microscopy, including in particular by scanning electron microscope SEM (preferably for the planar dimensions) and by focused ion beam FIB (preferably for the thickness and length dimensions). Macroparticles having an almost spherical shape are characterized by an aspect ratio of approximately 1:1, whereas flake-like particles can have an aspect ratio (e.g. between their length and their thickness, ASP=Lf/Tf) of 100:1 or more. Though not limiting, the macroparticles of swollen polymer matrix according to the present teachings can have an aspect ratio (or average aspect ratio considering a population of matrix flakes, $ASP_{avg}=Lf_{avg}/Tf_{avg}$) of about 100:1 or less, of about 75:1 or less, of about 50:1 or less, of about 25:1 or less, or even of about 10:1. In some embodiments, the matrix flakes according to the present teachings may have an aspect ratio (or average aspect ratio) of at least 3:1, at least 5:1, at least 10:1, at least 25:1, at least 40:1, or at least 70:1. In some embodiments, the macroparticles according to the present teachings may be flakes having an aspect ratio (or average aspect ratio) within a range of 2:1 to 500:1, 4:1 to 500:1, 8:1 to 500:1, 20:1 to 500:1, 20:1 to 300:1, 20:1 to 250:1, 20:1 to 200:1, or 20:1 to 100:1.

In some embodiments the nanoparticles of the UV-protective agent are homogeneously dispersed and embedded in the swelled polymer matrix macroparticles, such that the surface area of each such nanoparticle is fully encased in the swelled polymer matrix macroparticle. Preferably, the nanoparticles of UV-protective agent are sufficiently dispersed within the swelled polymer matrix macroparticles so as to prevent or reduce formation of clumps or aggregates of nanoparticles.

As the milling process which ensures the incorporation of the nanoparticles into the matrix polymer, and the size reduction of the latter to matrix macroparticles, is expected to at least further disperse the nanoparticles, it is believed that a population of nanoparticles well dispersed before their embedment in the polymer matrix will remain at least as well dispersed in the matrix elements. Nanoparticles of UV-protective agents fulfilling at least one or more of the size and/or size distribution criteria detailed in the preceding sections when present in the oil-dispersed stock are therefore expected to suitably disperse in the matrix macroparticles, providing for the sought "uniform dispersion" therein According to some embodiments, the dispersant may be any additive that increases the dispersability of the nanoparticles of UV-protective agent in at least one of the oil-dispersed stock to be added to the swollen polymer matrix in order to be co-milled and in the swelled polymer matrix macroparticles. In some embodiments, the dispersant comprises a carboxylic acid function to interact with oxide on the surface of the nanoparticles and a hydrocarbon portion, rendering the nanoparticles miscible in the macroparticles. In some preferred embodiments, the dispersant comprises fatty acids or polymers thereof.

In some embodiments, the dispersant has a Hydrophilic-Lipophilic Balance (HLB) value of no more than 9, no more than 6 or even no more than 3. In some embodiments, the HLB of the dispersant is about 2.5.

In some embodiments, the weight per weight ratio of dispersant to nanoparticles being dispersed therewith, is between 2:1 and 1:2. In a particular embodiment, the weight per weight ration of dispersant to nanoparticles of UV-protective agent is of about 1:1.

In some embodiments, the dispersant comprises polyhydroxystearic acid (available commercially from Innospec Performance Chemicals under tradenames Dispersun DSP-OL100 and DSP-OL300).

Other, non-limiting examples of suitable dispersants include any of the Pelemol esters, available commercially from Phoenix Chemicals, Overland Park, Kans., USA: Pelemol® BIP-PC (butylphthalimide and isoproplylphthalimide); Pelemol® C25EH (C12-15 alkyl ethylhexanoate); Pelemol® CA (cetyl acetate); Pelemol® 899 (isononyl isononanoate and ethylhexyl isononnoate); Pelemol® 168 (cetyl ehtylhexanoate); Pelemol® 256 (C12-C15 alkyl benzoate); Pelemol® 89 (ethylhexyl isononanoate); Pelemol® 3G22 (polyglyceryl-3 beherate); Pelemol® D5R1 (ethyl isonanoate and cetyl dimethicone); Pelemol® D5RV (propanediol dicaprylate/caprate and diisostearyl malate); Pelemol® D899 (PPG-26 dimer dilinoleate copolymer and isononyl isononanoate and ethylhexyl isononanoate); Pelemol® DD (dimer dilinoleyl dimer dilinoleate); Pelemol® DDA (diethylhexyl adipate); Pelemol® DO (decyl oleate); Pelemol® DP-72 (dipentaerythirityl tetrabehenate/poyhydroxystearate-lanolic substitute); Pelemol® EE (octyldodecyl erucate); Pelemol® G7A (glyceryl-7 triacetate); Pelemol® GMB (glyceryl behemate); Pelemol® GMR (glyceryl ricinoleate); Pelemol® GTAR (glyceryl triacetyl ricinoleate): Pelemol® GTB (tribehenin); Pelemol® GTHS (trihydroxystearin); Pelemol® GTIS (triisostearin); Pelemol® GTO (triethylhexanoin); Pelemol® ICB (isocetyl behenate); Pelemol® II (isostearyl isostearate); Pelemol® IN-2 (isononyl isonanoate); Pelemol® ISB (isostearyl behenate); Pelemol® ISHS (isostearyl hydroxystearate); Pelemol® ISNP (isostearyl neopentanoate); Pelemol® JEC (triisostearin/glyceryl behenate); Pelemol® MAR (methyl acetyl ricinoleate); Pelemol® NPGDD (neopentylglycol/dicaprate/dicaprylate); Pelemol® OL (oleyl lactate); Pelemol® OPG (ethylhexyl pelargonate); Pelemol® P-49 (pentaerylthrityl teraisononanoate); Pelemol® P-810 (propanediol dicaprylate/caprate); Pelemol® P-1263 (polyglycerol-10 hexaoleate and polyglyceryl-6 poyricinoleate); Pelemol® PHS-8 (polyhydroxystearic acid); Pelemol® PTIS (pentaerythrityl tetraisostearate); Pelemol® PTL (pentaerythrityl terralaurate); Pelemol® PTO (pentaerythrityl tetraethylhexanoate); Pelemol® SPO (cetearyl ethylhexanoate; Pelemol® TDE (tridecyl enucate); Pelemol® TGC (trioctyldodecyl citrate); Pelemol® TMPIS (trimethylolpropane triisostearate); Pelemol® TMPO (trimethylopropane triethylhexanoate); Pelemol® TT (tribeherin and caprylic acid/capric triglyceride); Pelemol® VL (dimer dilinoelyl dier dilinoleate and triisostearin).

In some embodiments, the dispersant is oleic acid, polyhydroxystearic acid (such as commercially available as Dispersun DSP-OL300 from InnoSpec or Pelemol® PHS-8 from Phoenix Chemicals), or octyldodecyl/PPG-3 myristyl ether dimer dilinoleate (such as commercially available as PolyEFA from Croda Inc.).

In some embodiments, the dispersant associated with the nanoparticles of inorganic crystal to ensure their adequate dispersion in the liquid oil before their incorporation into the polymer matrix, is the sole dispersant used in the composition. It is believed that the shape of the matrix macroparticles may affect the need to include further dispersants or increased amount of dispersant, at same or different steps. The Applicant found that matrix macroparticles having a tentacular flake shape loosely flocculate, so that advantageously no further dispersants are needed in compositions consisting of such matrix elements.

According to some embodiments, the solid inorganic crystal is doped, for example with a metal cation dopant such as iron, copper, manganese or lanthanum As used herein, the term "dopant" refers to cations, such as metal cations, which are introduced in low amounts into a crystalline structure.

In some embodiments the doped solid inorganic crystal comprises from about 90% or even from 95% to about 99.9% mole percentage solid inorganic material and from about 0.1% to about 5% or even 10% mole percentage of a metal cation as a dopant.

In some embodiments, the composition further comprises silver metal particles. In some embodiments, the silver particles are dispersed in the matrix elements.

In some embodiments, the silver metal particles are present in the composition as nanoparticles. In some embodiments, the silver nanoparticles have a length of up to about 50 nm. In some embodiments, the silver nanoparticles have at a length of up to about 40 nm. In some embodiments, the silver nanoparticles have a length of up to about 30 nm. In some embodiments, the silver nanoparticles have a length in the range of from about 10 nm to up to about 50 nm.

In some embodiments, the afore-mentioned dimensions or ranges of dimensions apply to at least 50%, or at least 55%, or at least 60%, or at least 65%, or at least 70%, or at least 75%, or at least 80%, or at least 90%, at least 95%, or at least 97.5% or at least 99% of the population of the silver nanoparticles.

In some embodiments, the aforesaid length of the silver nanoparticles is estimated based on the hydrodynamic diameter of the particles as measured by DLS techniques. In some embodiments, the population distribution of the silver nanoparticles is expressed in terms of the cumulative particle size distribution according to the number of particles in a sample. In some embodiments, the population distribution of the silver nanoparticles is expressed in terms of the cumulative particle size distribution of a sample volume of particles.

In some embodiments, the silver nanoparticles are present in the composition at a concentration in the range of from about 0.01% to about 10% (w/w) of the total composition. In some embodiments, the silver nanoparticles are present in the composition at a concentration in the range of from about 0.01% to about 5% (w/w), from about 0.05% to about 5% (w/w), or from about 0.1% to about 2% (w/w) of the total composition. In some preferred embodiments, the silver nanoparticles are present in the composition at a concentration of about 1% (w/w) or about 2% (w/w) of the total composition.

In some embodiments, the UV-protective composition comprises a topical composition. The topical composition may optionally be provided in a form selected from the group consisting of a cream, an emulsion, a gel, a lotion, a mousse, a paste and a spray. If desired, the composition can also be formulated into make-up cosmetics, for example, foundation, blusher, etc.

In some embodiments, the topical UV-protective composition further comprises a dermatologically or cosmetically or pharmaceutically acceptable carrier.

In some embodiments, the topical UV-protective composition further comprises one or more dermatologically or cosmetically or pharmaceutically acceptable additives or excipients, such as colorants, preservatives, fragrances, humectants, emollients, emulsifiers, waterproofing agents, surfactants, thickeners, viscosity modifiers, anti-foaming agents, conditioning agents, antioxidants and the like. Such additives or excipients and the concentrations at which each can effectively accomplish its respective functions, are known to persons skilled in the pertinent art and need not be further detailed.

In some embodiments, the composition is formulated for application to a surface of an inanimate object, such as, for example, an object, or a material. In some such embodiments, the composition is in the form of a coating, including liquid coatings, such as a varnish, a lacquer or an emulsion, and non-liquid coatings, such as a paste, a gel, or a mousse.

In another aspect of the present disclosure, there is provided a method for the preparation of the compositions disclosed herein. In some embodiments, the method comprises combining the thermoplastic polymer with the swelling agent, such as an oil; mixing the combination of thermoplastic polymer and swelling agent to provide a homogeneous paste of polymer matrix wherein the thermoplastic polymer is swelled with the swelling agent; adding the nanoparticles of UV-protective agent to the homogeneous paste, the inorganic nanoparticles being dispersed in an oil that may be same or different to the swelling agent previously combined with the thermoplastic polymer; and milling the mixture of the oil-dispersed nanoparticles and swollen polymer, so as to size reduce the polymer matrix into swelled polymer matrix macroparticles, while dispersing and embedding the nanoparticles of UV-protective agent in the swelled polymer matrix macroparticles.

Figure 11:
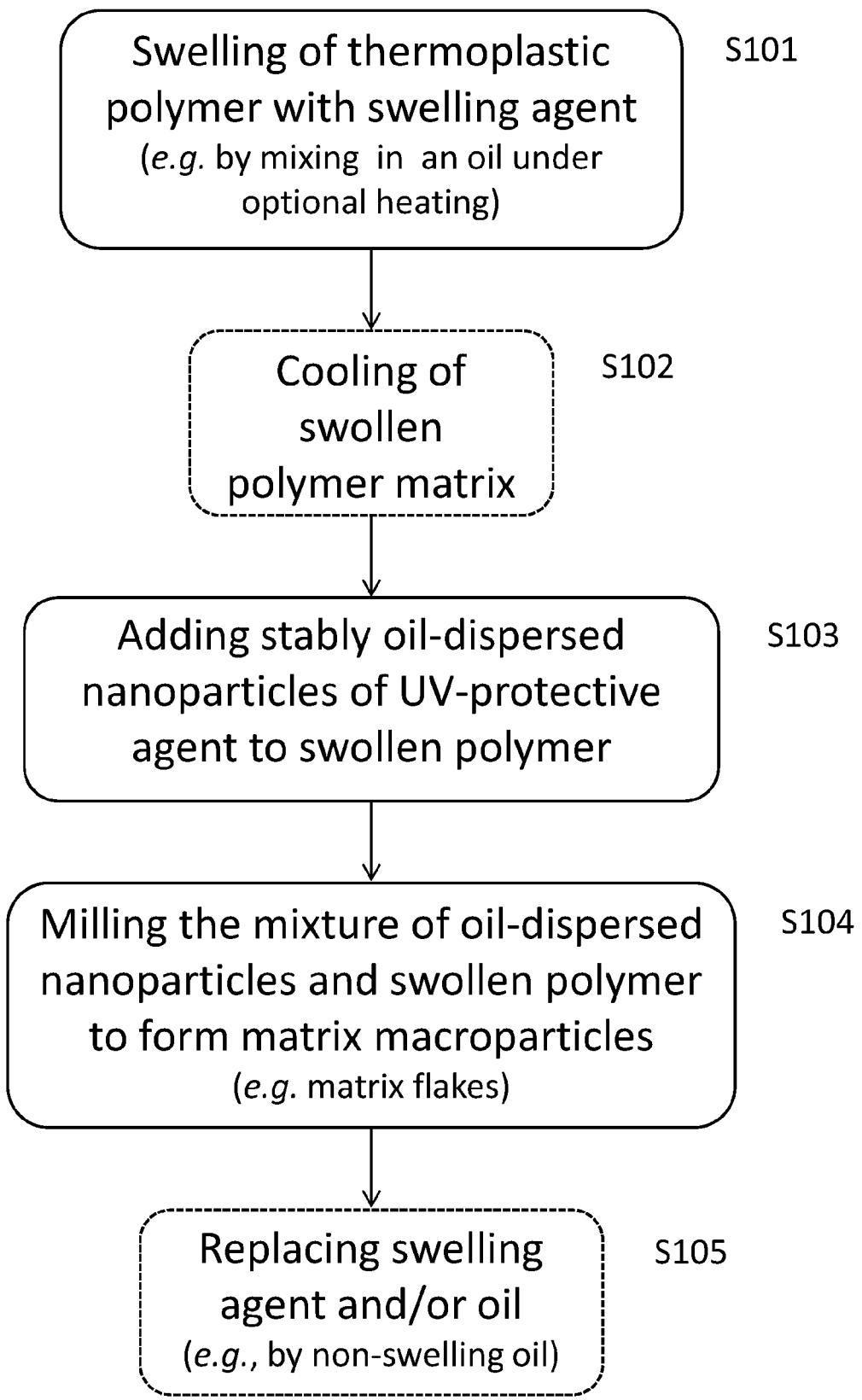
FIG. 11 provides a flow chart of one method according to the present teachings.

In some embodiments, the swelling agent and/or the first oil having served for the dispersion of the nanoparticles (or mixtures of any of the foregoing liquids) are at least partially replaced by a different second oil. In such a case, matrix elements having a first softening temperature when associated with the swelling agent(s) and/or first oil(s) can be tailored to have a different second softening point following such partial replacement. Preferably, the second softening point is greater than the first softening point, and optionally greater than 50° C. For such purpose, the replacing oil can be selected to fulfil at least one of the following conditions: a) it cannot swell the thermoplastic polymer under consideration (e.g., resulting in a gain weight of less than 1 wt. %); and b) it does not act as a plasticizer towards the thermoplastic polymer under consideration (e.g., it does not lower the softening point of the polymer). Such at least partial replacement can be performed by evaporation of the liquid embedded in the matrix elements (e.g., under vacuum for volatile oils), resulting in relatively dried macroparticles. At least part of the weight loss resulting from the partial elimination of the original liquid(s) can be compensated by addition of the second oil, which may serve to redisperse the relatively dried matrix elements having consequently a higher softening point. Such optional step is represented by S105 in FIG. 11.

In some embodiments, the nanoparticles of the UV-protective agent are milled prior to their addition to the polymer paste. The nanoparticles of UV-protective agent can be size-reduced in an oil that may be the same or different from the swelling agent with which the thermoplastic polymer is combined to provide the homogeneous paste. In some embodiments, the particles of UV-protective agent are milled, optionally in presence of a dispersant, so as to form nanoparticles. Alternatively, the particles of UV-protective agent being added are commercially available as nanoparticles or will be size-reduced to become nanoparticles subsequent to their addition to the oil-polymer paste.

In some embodiments, the mixing of the thermoplastic polymer and the swelling agent, such as an oil is performed while heating the combination to a temperature of from about 0° C. to about 20° C. above the melting point or the softening point of the thermoplastic polymer, or of up to about 30° C., or up to about 40° C. above the melting or softening point, as appropriate for the thermoplastic polymer.

In some embodiments, the homogenous paste of swollen polymer is cooled below the melting point or softening point of the thermoplastic polymer In some embodiments, the swelling agent-polymer paste (aka, the polymer matrix or swelled polymer matrix) is allowed to cool to ambient temperature (about 23° C.) or less before adding the nanoparticles of UV-protective agent.

In some embodiments, milling of the homogenous paste with the nanoparticles of UV-protective agent is performed while maintaining the mixture below the melting point or softening point of the thermoplastic polymer.

In some embodiments, the method further comprises, subsequent to adding the nanoparticles of UV-protective agent, milling the paste to provide swelled polymer matrix macroparticles having a length or a flake length (Lf) of up to about 50 µm.

The swelled polymer matrix macroparticles can have any suitable shape, and may for example be in the form of flakes, rods, or spheres.

In some preferred embodiments, at least 50% of the swelled polymer matrix macroparticles are flakes. It is believed that flakes provide better packing and coverage when applied on a surface to protect the surface from a harmful effect of UV irradiation.

As used herein, the term "flake" refers to a particle, in particular a macroparticle, having a flake length (Lf), a flake width (Wf), and a flake thickness (Tf), wherein the flake aspect ratio (Rf) is defined by:

$$Rf = (Lf \cdot Wf)/Tf^2$$

and wherein Rf is at least 5, at least 10, at least 15, at least 20, at least 25, at least 30, at least 50, at least 100, at least 150, at least 250, or at least 500, and optionally, at most 2000, at most 1500, at most 1000. Said flake aspect ratio can be determined on a representative group of flakes, the group consisting of at least 10 flakes.

According to some embodiments, the flake aspect ratio (Rf) is within a range of 5 to 2000, 10 to 1000, 12 to 500, 12 to 200, or 15 to 100.

According to some embodiments, the flake thickness (Tf) of the macroparticle is at most 400 nm, at most 350 nm, at most 300 nm, at most 275 nm, at most 250 nm, or at most 225 nm.

Figure 10:
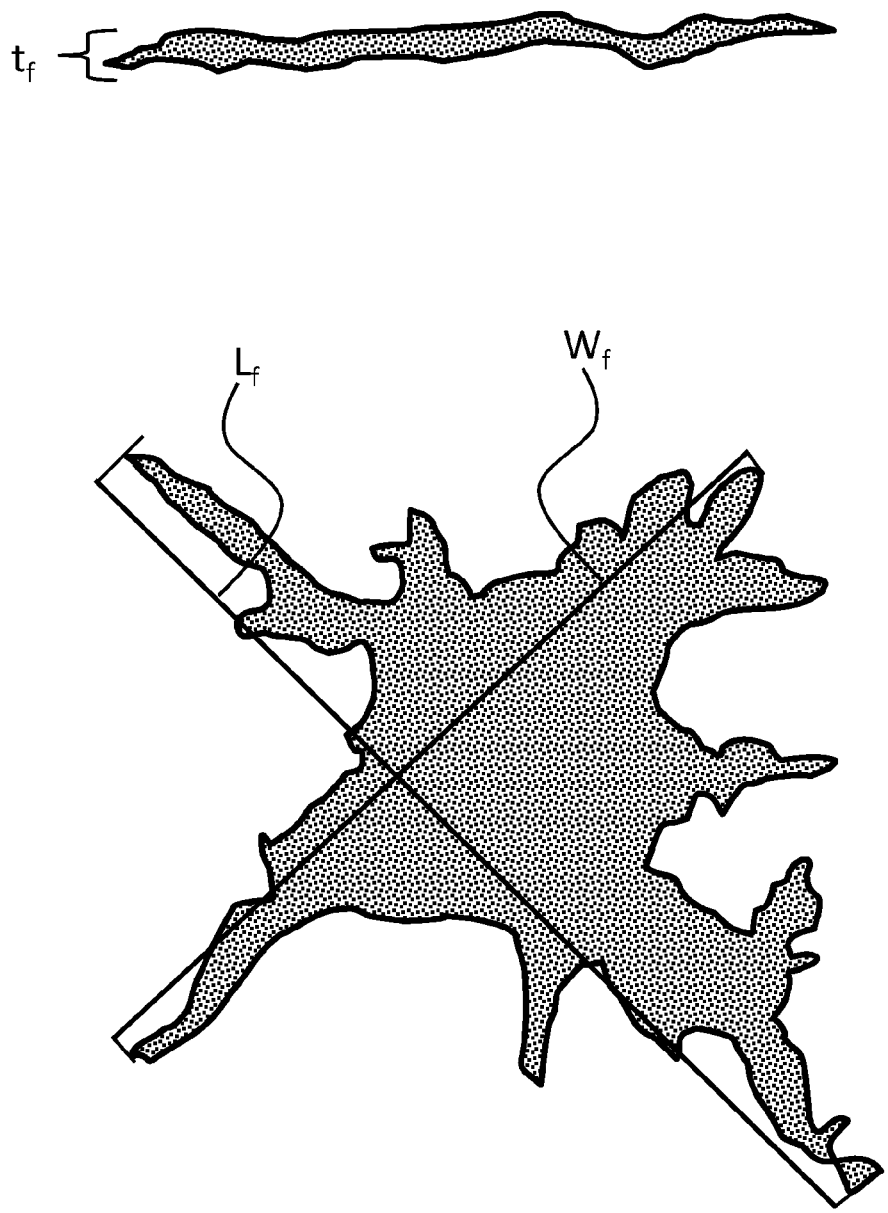
FIG. 10 schematically illustrate a cross-sectional and a top view of a swelled polymer matrix macroparticle having a tentacular flake shape.

FIG. 10 schematically illustrates a matrix flake and such characteristic measures are shown, on a cross sectional view and on a top view of the flake. The exemplary flake shown in this figure illustrates the particular case of a tentacular flake having a "core" body from which more narrow appendices extend.

Advantageously, the method according to the present teachings can provide for swelled polymer matrix macroarticles in the form of flakes, such flakes being optionally tentacular flakes. Without wishing to be bound by any particular theory, it is believed that nanoparticles of a UV-protective agent embedded in polymer matrix macroparticles shaped as flakes, and preferably uniformly dispersed therein, can provide significantly better protection than similar particles if merely entrapped in amorphous chunks of polymer or externally coating such polymeric core.

This is illustrated in FIG. 9, where panel A schematically shows a cross-sectional view of an example of conventionally prepared UV-protective polymers on a target surface. In this example, the particles of a UV-protective agent even, if somehow entrapped in the polymer by typical agitation techniques, generally reside in relatively large and amorphous chunks of polymers. By such method the particles of UV-protective agent are unlikely to be uniformly dispersed within the polymer matrix. Moreover, the conventional chunks would not be expected to be evenly spread on the surface to be protected, due to their disadvantageous shape. Therefore, as schematically illustrated in the perspective top view of panel B, the particles would remain on the target surface as irregularly distributed clusters. Understandingly, such distribution leaves unprotected areas and the scattering that may result from the clusters of particles of UV-protective agent may additionally reduce the efficacy of the composition even in the areas bearing some of the UV-protective agent.

Figure 9A:
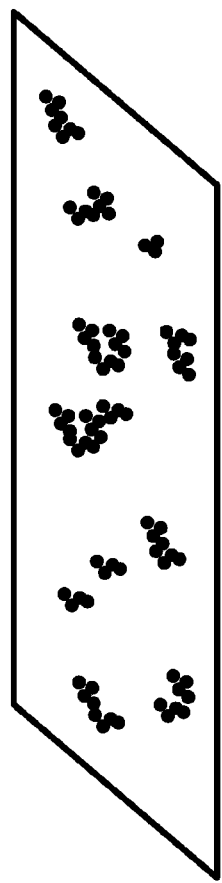
FIG. 9A schematically illustrates a cross sectional view on a surface of an example of conventionally prepared UV-protective polymers.
Figure 9B:
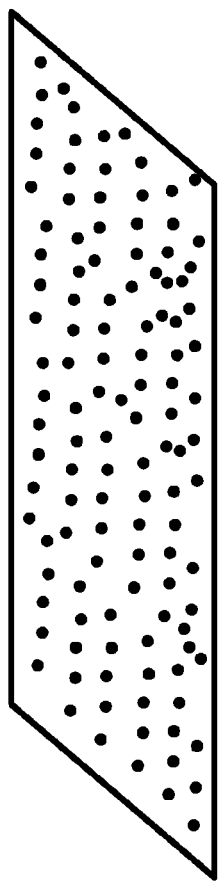
FIG. 9B schematically illustrates in a perspective top view how UV-protective particles entrapped in polymers as shown in FIG. 9A could remain on the target surface.
Figure 9C:
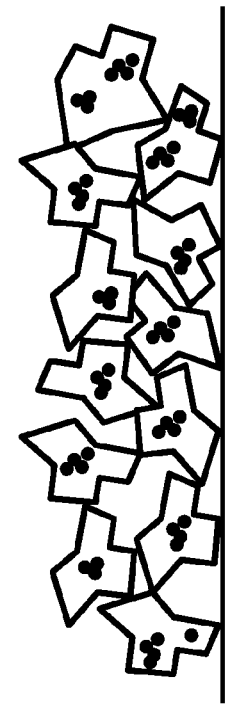
FIG. 9C schematically illustrates in a cross-sectional view how particles of a UV-protective agent embedded in swelled polymer matrix macroparticles, such as flakes, may be applied to a target surface.
Figure 9D:
FIG. 9D provides a schematic, perspective top view of UV-protective particles embedded and dispersed in swelled polymer matrix macroparticles as shown in FIG. 9C.

FIG. 9C schematically illustrates how particles of a UV-protective agent may be embedded and distributed in swelled polymer matrix macroparticles, such as flakes, and how the latter may be suitably applied to a target surface, by virtue of their relatively flat shapes. The schematic top view of the same, FIG. 9D, shows how compositions of the invention are expected to provide at least one of a more uniform distribution of the nanoparticles of UV-protective agent within the matrix elements, a more uniform coverage of the target surface by the swelled polymer matrix macroparticles, a more uniform distribution of the nanoparticles of UV-protective agent on the target surface, a reduced light scattering and an improved protection against UV-radiation.

Additionally, the presence of one or more tentacles on a flake matrix element, as illustrated in the top view provided in FIG. 10, can facilitate the redispersion of matrix elements produced by the present method. As such, matrix elements may be sufficiently large to tend to separate from their carrier over time, the presence of extensions of the elements may serve to increase steric hindrance between neighbouring macroelements, so that any assembly of such elements would be loose and easily dispersible into individual elements upon mild agitation.

According to a further aspect of some embodiments of the disclosure, there is provided a UV-protective composition as disclosed herein, for use in protecting a subject, such as a human subject, against a harmful effect of ultraviolet radiation, in some embodiments providing broad-spectrum protection against both ultraviolet A and ultraviolet B radiation.

In some embodiments, the composition is for use in protecting the skin of a subject, against a harmful effect of ultraviolet radiation, in some embodiments providing broad-spectrum protection against both ultraviolet A and ultraviolet B radiation.

In some embodiments, the composition is for use in protecting the hair of a subject, such as a human subject, against ultraviolet radiation, in some embodiments against both ultraviolet A and ultraviolet B radiation.

According to a further aspect of some embodiments of the disclosure, there is provided a UV-protective composition as disclosed herein, for use in protecting an inanimate object, against a harmful effect of ultraviolet radiation, in some embodiments providing broad-spectrum protection against both ultraviolet A and ultraviolet B radiation.

There is also provided, in accordance with an embodiment of the invention, a method of protecting a surface from UV radiation, which comprises applying to a surface in need of such protection a UV-protective composition as described herein in an amount sufficient to achieve such protection. In some embodiments, the surface is human skin. In some embodiments, the surface is non-human skin, i.e. animal skin. In some embodiments, the surface is hair. In some embodiments, the hair is human hair. In some embodiments, the hair is non-human hair, i.e. animal hair. In some embodiments, the surface is a surface of an inanimate object.

According to a further aspect of some embodiments of the disclosure, there is provided a method of protecting the skin of a subject against ultraviolet radiation, the method comprising applying to the skin of the subject an efficacious amount of a UV-protective composition comprising swelled polymer matrix macroparticles (optionally flakes) comprising a thermoplastic polymer swelled with at least one swelling agent, such as an oil; and a plurality of nanoparticles of an inorganic UV-protective agent, each of the nanoparticles comprising at least one solid inorganic crystal and a dispersant associated with the crystal, the inorganic nanoparticles being dispersed and embedded in the swelled polymer matrix macroparticles.

In some such embodiments, the UV-protective composition can be in the form of a skin-care product suitable for skin application and/or at least temporary retention thereupon. According to a further aspect of some embodiments of the disclosure, there is provided a method of protecting the hair of a subject against ultraviolet radiation, the method comprising applying to the hair of the subject an efficacious amount of a UV protective composition as disclosed herein. In some such embodiments, the UV-protective composition can be in the form of a hair-care product suitable for hair application and/or at least temporary retention thereupon.

According to a further aspect of some embodiments of the disclosure, there is provided a method of protecting the surface of an inanimate object against ultraviolet radiation, the method comprising applying to the surface of the object an efficacious amount of a UV protective composition as disclosed herein. In some such embodiments, the UV-protective composition can be in the form of a coating product suitable for application to inanimate surfaces and/or at least temporary retention thereupon.

According to a further aspect of some embodiments of the disclosure, there is provided the use of swelled polymer matrix macroparticles (optionally flakes) comprising a thermoplastic polymer swelled with at least one swelling agent, such as an oil; and a plurality of nanoparticles of an inorganic UV-protective agent, each of the nanoparticles comprising at least one solid inorganic crystal and a dispersant associated with the crystal, the inorganic nanoparticles being dispersed and embedded in the swelled polymer matrix macroparticles, in the manufacture of a composition for protection of the skin and/or the hair of a subject against ultraviolet radiation.

According to a further aspect of some embodiments of the disclosure, there is provided the use of a swelled polymer matrix macroparticles (optionally flakes) comprising a thermoplastic polymer swelled with at least one swelling agent, such as an oil; and a plurality of nanoparticles of an inorganic UV-protective agent, each of the nanoparticles comprising at least one solid inorganic crystal and a dispersant associated with the crystal, the inorganic nanoparticles being dispersed and embedded in the swelled polymer matrix macroparticles, in the manufacture of a composition for protection of exterior surfaces of an inanimate object against ultraviolet radiation. The exterior surface may comprise the surface of any material, including, but not limited to glass, fabrics, leathers, woods, cardboards, metals, plastics, rubbers, ceramics and other structural materials.

In some embodiments, the subject is a human subject.

The skin may be the skin of the face, of the arms, of the legs, of the neck of the torso, or of any other area of the body that can be exposed to UV radiation.

In some embodiments, the sunscreen composition as disclosed herein is applied to the skin of the subject prior to or during exposure to UV radiation. Advantageously, the composition is at least temporarily retained thereupon. In some embodiments, the composition is reapplied every 10 hours, 9 hours, 8 hours, 7 hours, 6 hours, 5 hours, 4 hours, 3 hours, 2 hours or every hour during exposure to UV radiation.

In some embodiments, the sunscreen composition for protecting the hair of a subject against ultraviolet radiation is provided in a form selected from the group consisting of a cream, an emulsion, a gel, a lotion, a mousse, a paste and a spray. In some embodiments, the composition is provided in the form of a shampoo, a conditioner or a hair mask.

In some embodiments, the composition is to be applied to the hair for a fixed period of time (such as up to 1 minute, up to 2 minutes, up to 3 minutes, up to 4 minutes or up to 5 minutes, up to 10 minutes, up to 15 minutes, up to 20 minutes, up to 25 minutes or even up to 30 minutes prior to rinsing. In some embodiments, the conditioner or hair mask is for applying to the hair without rinsing, such that the conditioner or hair mask remains on the hair.

EXAMPLES

Materials and Methods
Materials
 A—Inorganic Materials
 Anatase titanium dioxide was purchased from Sigma-Aldrich.
 Barium titanate was purchased from Sigma-Aldrich.
 Bismuth oxide was purchased from Sigma-Aldrich.
 Bismuth vanadate (BiVO4, Sicopal® yellow L 1600) was purchased from BASF SE, Ludwigshafen, Germany.

Manganese doped (5% doping) zinc oxide was prepared as disclosed in PCT/IB2016/051701

Rutile titanium dioxide was purchased from Tayca Corporation, Chuo-ku, Osaka, Japan.

Zinc oxide was purchased from Sigma-Aldrich.

B—Organic Materials

Bynel® 2022, Bynel® 4157, Bynel® CXA 2002, Bynel® CXA E214, Bynel® CXA 3036, Bynel® CXA 3048, Bynel® CXA 3095, Bynel® CXA 3101, Bynel® CXA 4109, Bynel® CXA 41E687, Bynel® CXA E-326, Bynel® CXA E-369, Bynel® CXA E-374, Elvax® 460, Elvax® 550, Elvax® 650, Elvax® 660, Elvax® 760, Elvax® 770, Nucrel® 0407, Nucrel® 0609, Nucrel® 699, Nucrel® 0903, Nucrel® 0908, Nucrel® 0910, Nucrel® 925, Nucrel® 1202, Nucrel® 2940, Nucrel® 30707, Nucrel® 31001, Surlyn® 1554, Surlyn® 1652, Surlyn® 1702, Surlyn® 1801, and Surlyn® 9910, all thermoplastic polymers, were purchased from E.I. du Pont de Nemours and Company, Wilmington, Del., USA.

Dispersun® DSP-OL300 (polyhydroxystearic acid) was purchased from InnoSpec Performance Chemicals.

Oleic acid was purchased from Sigma-Aldrich.

Isopar® L (CAS 64742-48-9 isoparaffinic fluid) was purchased from Parchem, New Rochelle, N.Y., USA.

Lotader® 2308, Lotader® 2400, Lotader® 3200, Lotader® 3210, Lotader® 3300, Lotader® 3410, Lotader® 6200, Lotader® 8200, and Lotader® TX 8030, all thermoplastic polymers, were purchased from Arkema, France.

Pelemol® 256 (C12-15 alkyl benzoate) oil, was purchased from Phoenix Chemicals, Overland Park, Kans., USA.

Pelemol® PHS-8 (vegetable-derived polyester) dispersant was purchased from Phoenix Chemicals, Overland Park, Kans., USA.

PolyEFA (octyldodecyl/PPG-3 myristyl ether dimer dilinoleate) dispersant was purchased from Croda Inc.

Equipment

High Resolution Scanning Electron Microscope Magellan XHR 400L FE-SEM by Nanolab Technologies, Albany, N.Y., USA.

Particle Size Analyser (Light Scattering) Zen 3600 Zetasizer by Malvern Instruments, Malvern, UK.

Oven, Vulcan-Hart 3-1750 multi-stage programmable box furnace.

Temperature controllable circulating water bath, BL-30L 9 liter ½HP by MRC, Hampstead, London, UK.

Grinding Mill Model HD-01 Attritor by Union Process®, Inc., Akron, Ohio, USA.

Analytical Balance XSE by Mettler-Toledo International Inc., Columbus, Ohio, USA.

Mortar Grinder PULVERISETTE 2 by Fritsch, Idar-Oberstein, Germany.

Double Planetary Mixer by Charles Ross & Son Company, Hauppauge, N.Y., USA.

Zirconia beads by PingXiang Lier Ceramic Co., Ltd., PingXiang Park Road, China.

Zirconia Yttria 3/16" beads by Glen Mills Inc., Clifton, N.J., USA.

Example 1

Preparation of Nanoparticles of UV-protective Agent

Nanoparticles of UV-protective agent comprising at least one solid crystal (crystals of titanium dioxide or bismuth vanadate) were prepared from titanium dioxide or bismuth vanadate stock powders, respectively. Generally, such stock powders contained particles having a size of greater than about 5 μm, and may be referred to hereinafter as the coarse powders. The coarse powders were milled in an Attritor grinding mill using a batch size of 200 g with solid loading 10% (20 g) as follows.

All materials were weighed using an analytical scale. 20 g of dispersant (Pelemol® PHS-8, unless otherwise indicated) was weighed and dispersed in about 100 ml of deionized water. 20 g of titanium dioxide or bismuth vanadate coarse powder was weighed and introduced into the dispersant-containing liquid to provide a dispersant to inorganic material ratio of 1:1 (w/w) yielding a slurry of the inorganic material. 160 g of $C_{12}$-$C_{15}$ alkyl benzoate as an oil were added. Water was added to complete batch size to 200 g, the inorganic material thereby constituting about 10 wt. % of the sample.

The slurry of solid inorganic crystals in oil was then placed in a zirconia pot with 2300 g of 2 mm diameter zirconia grinding beads. The pot was placed in the grinding mill, and the grinding mill activated at 700 RPM for 100 hours at 25° C. It is to be noted that the inorganic UV-protective agents herein contemplated are all classified as relatively hard materials, with a Mohs hardness of no less than about 4 (e.g., bismuth vanadate) and of up to at least about 7 (e.g., titanium dioxide). Such hardness levels can alternatively be provided on the Knoop scale where these materials display hardness numbers between 300 and 1000.

After 100 hours of milling, the hydrodynamic diameter of the nanoparticles was determined by Dynamic Light Scattering, using a Zen 3600 Zetasizer particle size analyzer. A sample of the milled nanoparticles was further diluted in Isopar® L to form a suspension having a solid inorganic concentration of about 0.1 wt. % for the sake of such measurements.

Representative results, showing the percentage of number of titanium dioxide or bismuth vanadate particles having hydrodynamic diameters in the range of 1-1000 nm are presented in FIG. 1.

As shown in FIG. 1, the nanoparticles of solid inorganic crystals in suspension had hydrodynamic diameters of up to about 100 nm. The majority of bismuth vanadate nanoparticles had hydrodynamic diameters in the size range of from about 20 nm and up to about 80 nm, with a predominant peak around about 30 nm. The majority of titanium dioxide nanoparticles had hydrodynamic diameters in the size range of from about 30 nm and up to about 100 nm, with a predominant peak around about 50 nm. Results of the particle size distribution of the nanoparticles prepared as herein described, namely the maximum hydrodynamic diameter of a percentage of the population, are provided in the Table 1 below, in terms of percent of number of particles.

TABLE 1

| | Max. Hydrodynamic Diameter | | | |
|---|---|---|---|---|
| Material | 90.0% | 95.0% | 97.5% | 99.0% |
| BiVO$_4$ | 41.9 nm | 48.5 nm | 55.6 nm | 65.7 nm |
| TiO$_2$ | 78.6 nm | 93.8 nm | 114 nm | 149 nm |

As can be seen in Table 1 at least 95% of the nanoparticles of titanium dioxide have a hydrodynamic diameter (hence a characteristic dimension) of at most 100 nm, while at least 99% of the nanoparticles of bismuth vanadate have a hydrodynamic diameter not exceeding 100 nm. Such results illustrate the preparation of particles having an average particle size, in the present case assessed by their hydrodynamic diameter, well below 100 nm, the present samples even comprising at least 90% of nanoparticles not exceeding about 80 nm.

Additional nanoparticles were prepared according to the same method, with oils and/or dispersants as indicated in Table 2 below in which the size distribution of the resulting particles (size being given in nanometers, as well as the standard deviation of the peak) is provided in terms of percent of number of particles of UV-protective agent. The polydispersity index (PDI), which is a measure of the width of the particle size distribution, is unit-less, indices of less than 0.4 being considered suitable, indices of less than 0.2 or even 0.1 referring to particularly narrow "monodisperse" populations of nanoparticles.

TABLE 2

| Inorganic Material | Oil | Dispersant | $D_N10$ | $D_N50$ | $D_N90$ | STD | PDI |
|---|---|---|---|---|---|---|---|
| Anatase TiO$_2$ | C12-15 | Pelemol® PHS-8:PolyEFA (1:1) | 54.7 | 77.2 | 136 | 37.1 | 0.13 |
| Anatase TiO$_2$ | C12-15 | Bynel® 2200 | 50.9 | 69.8 | 114 | 29.8 | 0.13 |
| Barium Titanate | C12-15 | Pelemol® PHS-8 | 38.0 | 52.0 | 80.3 | 18.7 | 0.16 |
| Bismuth Oxide | C12-15 | Pelemol® PHS-8 | 29.9 | 40.6 | 61.2 | 14.6 | 0.34 |
| Bismuth Oxide | Isopar® L | Pelemol® PHS-8 | 35.5 | 47.9 | 71.5 | 15.7 | 0.18 |
| Bismuth Vanadate | C12-15 | Pelemol® PHS-8 | 24.8 | 33.9 | 51.3 | 11.9 | 0.22 |
| Rutile TiO$_2$ | C12-15 | Pelemol® PHS-8 | 38.6 | 52.4 | 78.6 | 17.4 | 0.15 |
| Zinc Oxide | C12-15 | Dispersun DSP-OL300 | 86.0 | 138.0 | 253 | 66.9 | 0.19 |
| Zinc Oxide | Isopar® L | Oleic acid | 68.6 | 100 | 200 | 57.4 | 0.17 |
| ZnO—Mn doped | C12-15 | Pelemol® PHS-8 | 37.6 | 51.2 | 78.9 | 18.6 | 0.36 |

Example 2

Selection of Swellable Polymers

In order to assess the swellability of thermoplastic polymers by a swelling agent of interest, a known amount of polymer (generally in the form of beads, as provide by suppliers) was weighted, immersed in an excel amount of oil and incubated for a predetermined duration at any desired temperature. The resulting mixture, preferably including a swollen polymer, was allowed to filter through a mesh to remove excess oil not absorbed by the polymer. The so isolated polymer matrix was weighted, and the amount of weight gain was calculated, typically in percentage of original weight.

In one experiment, 30 g of polymers were immersed in about 100 ml of Isopar™ L (high purity synthetic isoparaffin fluid) and left to incubate for 4 days at 50° C. The weight gains (% of native polymer weight) are reported in Table 3 below, as well as the melting temperature ($T_m$) and/or softening temperature ($T_s$) in degrees Celsius, as provided by the supplier based on thermal analysis. The reported melting points were generally determined according to ASTM D3418 and the reported softening points according to ASTM D1525.

TABLE 3

| Material | Supplier | % Weight Gain | $T_m$ | $T_s$ |
| --- | --- | --- | --- | --- |
| Bynel ® 2022 | Du Pont | 52.61 | 87° C. | 58° C. |
| Bynel ® 4157 | Du Pont | 26.86 | 127° C. | 93° C. |
| Bynel ® CXA 2002 | Du Pont | 47.01 | 91° C. | 60° C. |
| Bynel ® CXA 3036 | Du Pont | 82.19 | | |
| Bynel ® CXA 3048 | Du Pont | 33.80 | | |
| Bynel ® CXA 3095 | Du Pont | 34.35 | | |
| Bynel ® CXA 3101 | Du Pont | 81.43 | 87° C. | 65° C. |
| Bynel ® CXA 4109 | Du Pont | 27.09 | | |
| Bynel ® CXA 41E687 | Du Pont | 30.41 | 119° C. | 84° C. |
| Bynel ® CXA 214 | Du Pont | 78.64 | | |
| Bynel ® CXA E-326 | Du Pont | 89.98 | | |
| Bynel ® CXA E-369 | Du Pont | 106.66 | | |
| Bynel ® CXA E-374 | Du Pont | 112.73 | | |
| Elvax ® 460 | Du Pont | 80.41 | 88° C. | 64° C. |
| Elvax ® 550 | Du Pont | 53.50 | 85° C. | 62° C. |
| Elvax ® 650 | Du Pont | 43.44 | 95° C. | 65° C. |
| Elvax ® 660 | Du Pont | 39.03 | 96° C. | 74° C. |
| Elvax ® 760 | Du Pont | 31.03 | 100° C. | 82° C. |
| Elvax ® 770 | Du Pont | 33.71 | 96° C. | 80° C. |
| Lotader ® 2308 | Atochem | 65.26 | 112° C. | 65° C. |
| Lotader ® 2400 | Atochem | 46.76 | | |
| Lotader ® 3200 | Atochem | 20.36 | 107° C. | 80° C. |
| Lotader ® 3210 | Atochem | 24.31 | 107° C. | 76° C. |
| Lotader ® 3300 | Atochem | 29.29 | 98° C. | 70° C. |
| Lotader ® 3410 | Atochem | 58.57 | 89° C. | 47° C. |
| Lotader ® 6200 | Atochem | 27.21 | 102° C. | 70° C. |
| Lotader ® 8200 | Atochem | 32.24 | 100° C. | 61° C. |
| Lotader ® TX 8030 | Atofina | 42.11 | 95° C. | 65° C. |
| Nucrel ® 0407 ACR | Du Pont | 21.89 | 110° C. | 90° C. |
| Nucrel ® 0609 HAS | Du Pont | 21.26 | 104° C. | 88° C. |
| Nucrel ® 0609 HS | Du Pont | 21.58 | | |
| Nucrel ® 0903 | Du Pont | 21.08 | 101° C. | 81° C. |
| Nucrel ® 0903 HS | Du Pont | 24.36 | | |
| Nucrel ® 0903 B | Du Pont | 21.17 | | |
| Nucrel ® 0908 HS | Du Pont | 21.84 | 100° C. | 80° C. |
| Nucrel ® 0910 HS | Du Pont | 23.34 | 103° C. | 86° C. |
| Nucrel ® 1202 | Du Pont | 23.81 | 99° C. | 75° C. |
| Nucrel ® 699 | Du Pont | 21.80 | 94° C. | 65° C. |
| Nucrel ® 925 | Du Pont | 28.14 | 92° C. | 67° C. |
| Nucrel ® 2940 | Du Pont | 42.41 | 83° C. | 48° C. |
| Nucrel ® 30707 | Du Pont | 20.33 | 102° C. | 84° C. |
| Nucrel ® 31001 | Du Pont | 23.57 | 99° C. | 79° C. |
| Primacor ® 3440 | Dow | 25.47 | 98° C. | 81° C. |
| Surlyn ® 1554 | Du Pont | 22.33 | | |
| Surlyn ® 1652 | Du Pont | 22.64 | 100° C. | 79° C. |
| Surlyn ® 1702 | Du Pont | 28.43 | 93° C. | 65° C. |
| Surlyn ® 1801 | Du Pont | 23.15 | | |
| Surlyn ® 9910 | Du Pont | 23.67 | 86° C. | 62° C. |

As can be seen from the above-table, a variety of thermoplastic polymers may be swellable, namely gaining at least 20% in weight under present experimental conditions, the oil Isopar™ L being but an example of such swelling agents.

Preferably the swollen polymer matrix should retain a sufficiently high softening point and/or melting point once combined with an oil that may serve as a plasticizer to the polymer. The softening and/or melting temperature of the swelling polymer mixture or swollen polymer matrix can be determined by DSC by routine procedures.

The softening point of the polymer matrix including about 22 wt. % of oil swelled into Nucrel® 699 polymer was determined by thermal analysis on a range of 25 to 150° C. at a rate of 10° C./min in a DSC Q2000 of TA Instruments. While a control of native polymer displayed a set-off transition temperature at about 88° C., with a peak of about 100° C. (the $T_m$ provided by the supplier being of about 94° C.), the swollen matrix displayed decreased temperatures of about 74° C. for the set-off transition and about 90° C. for the peak, suggesting that Isopar™ L acts as a plasticizer for this polymer.

Example 3

Preparation of Swelled Polymer Matrix Macroparticles 25 g of Nucrel® 699 polymer beads (copolymer of ethylene and methacrylic acid, having a melting point of 94° C., a softening point of 65° C., and having been found swellable according to Example 2) were added to 75 g Isopar™ L (high purity synthetic isoparaffin fluid) to provide a suspension of polymer beads in oil. The suspension was placed in the double planetary mixer and heated to a temperature of about 100° C. with a hot water bath circulator, and mixed for about 4 hours, until a homogeneous soft white paste of oil swelled polymer was obtained. The paste was then allowed to cool for about 12 hours at room temperature, with constant mixing. The resulting paste was further processed as described in Example 4.

Example 4

Preparation of Composition Comprising Swelled Polymer Matrix Macroparticles and Nanoparticles UV-protective Agent 4 weight portions of the swelled polymer matrix, prepared as described in Example 3 (consisting of Nucrel® 699 and Isopar™ L) were mixed with 1 weight portion of the inorganic nanoparticles of UV-protective agent prepared as described in Example 1, the nanoparticles being oil-dispersed with a dispersant. 50-100 g Isopar™ L were added to the mixture of swelled polymer matrix and inorganic nanoparticles to give a final weight of 200 g.

200 g of the resulting mixture were placed in a Zirconia pot, 2,500 g of Zirconia 3/32" diameter beads were added to the pot, and the pot was placed in the grinding mill.

The temperature of the pot was maintained at 25° C. while the grinding mill was set to mill the contents of the pot at 700 rpm for 12 hours resulting in a composition according to the teachings herein comprising inorganic nanoparticles of UV-protective agent dispersed and embedded in the swelled polymer matrix macroparticles.

Figure 2:
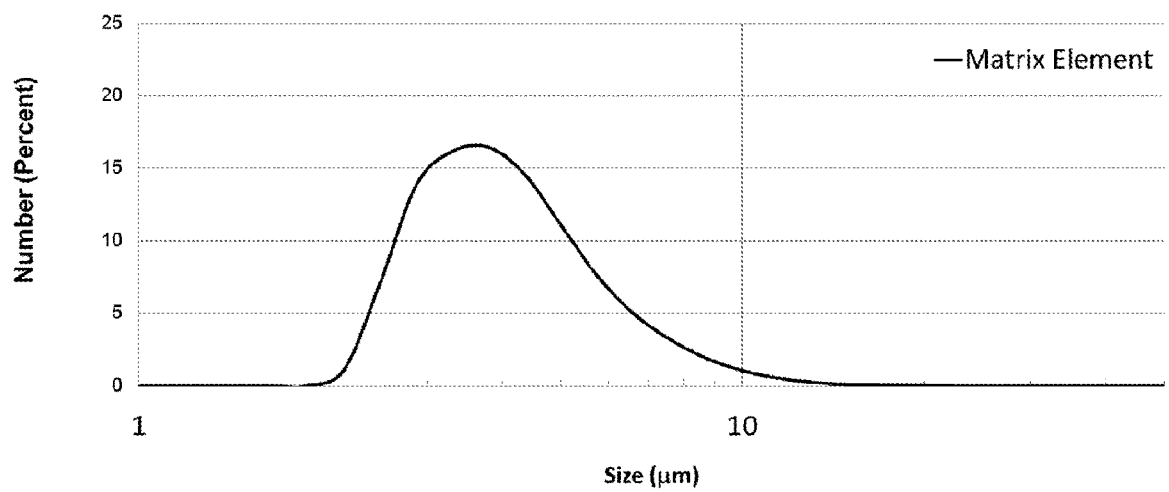
FIG. 2 is a line graph showing Particle Size Distribution (PSD) of swelled polymer matrix macroparticles after milling, expressed as number percentage.

Hydrodynamic diameters of the resulting macroparticles were determined as described above. The percentage (per number) of swelled polymer matrix macroparticles having hydrodynamic diameters in the range of 1-50 µm are presented in FIG. 2. As shown in FIG. 2, the matrix macroparticles obtained by this process had hydrodynamic diameters of up to about 10 µm. The majority of swelled polymer matrix macroparticles had hydrodynamic diameters in the size range of from about 3 µm and up to about 10 µm, with a predominant peak around about 4 µm. Microscopic analysis detailed below determined that the shape of the resulting matrix elements was flake-like.

Example 5

Absorbance of Oil-dispersed Titanium Dioxide and Bismuth Vanadate Nanoparticles

Absorbance of titanium dioxide and bismuth vanadate nanoparticles over the wavelength range of 200-800 nm was measured using a Cary 300 UV-Vis spectrophotometer with quartz cuvette (10 mm light pathway). The fluid carrier in which the inorganic materials were milled as described in Example 1 (namely the C12-C15 oil and the dispersant was diluted to the same extent as the nanoparticles (e.g., to provide a solid concentration of 0.1 wt. %). The diluted fluid carrier, free of nanoparticles, was included as reference for comparative purpose. Results are presented in FIG. 3.

Figure 3:
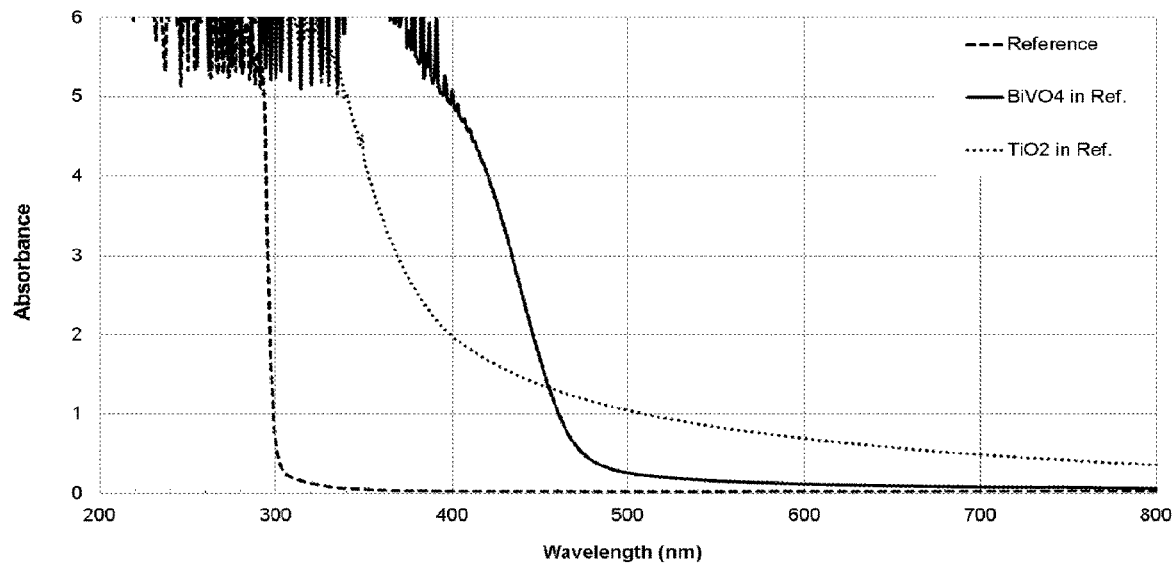
FIG. 3 is a line graph showing absorbance of bismuth vanadate and titanium dioxide nanoparticles alone, prior to their incorporation into the swelled polymer matrix macroparticles of the present disclosure, with a reference comprising the medium in which milling to produce nanoparticles was carried out, i.e. C12-15 oil and dispersant, with Isopar™ L as diluent.

As seen in FIG. 3, absorbance in the 280-400 nm wavelength range was shown for both titanium dioxide and bismuth vanadate, in a pattern clearly distinct from the reference having no significant absorbance in this wavelength range.

Example 6

Absorbance of Titanium Dioxide and Bismuth Vanadate Nanoparticles Dispersed and Embedded in Swelled Polymer Matrix Macroparticles As the compositions prepared in accordance with Example 4 are no longer suitable for assessment of absorbance as diluted suspensions, a dry thin film of the compositions was prepared as follows. A standard glass microscope slide was provided as a support. The slide was placed on a flat polytetrafluoroethylene surfaces and the two ends of the slide were covered with strips of 50 micrometer thick adhesive tape. A glass rod was used to evenly smear 200 mg of the matrix element particles on the glass slide between the two strips of adhesive tape. The glass slide with the smeared matrix element particles was placed in an oven maintained at 50° C. for 4 hours, following which time the two strips of adhesive tape were removed. The glass slide was then placed (composition side up) on a hot plate having a temperature of 100° C. for 30 seconds and a second glass slide was then placed on the heat softened composition. The glass slide was allowed to cool to room temperature, following which the cover slide was removed exposing a dry thin film of the composition under study. Under such sample preparation conditions, the nanoparticles of UV-protective agent embedded in the matrix elements remain relatively immobilized within their respective matrix elements Films prepared by this method typically had a uniform thickness of about 6 µm as measured by a LEXT confocal laser scanning microscope (Olympus Corporation).

Absorbance of titanium dioxide and bismuth vanadate nanoparticles dispersed and embedded in the swelled polymer matrix macroparticles, over the wavelength range of 200-800 nm was measured by placing glass slides coated with a thin film of the compositions in a Cary 300 UV-Vis spectrophotometer. An uncoated glass slide and one coated solely with the matrix element particles devoid of the inorganic nanoparticles were included as references for comparative purpose. Results are presented in FIG. 4.

Figure 4:
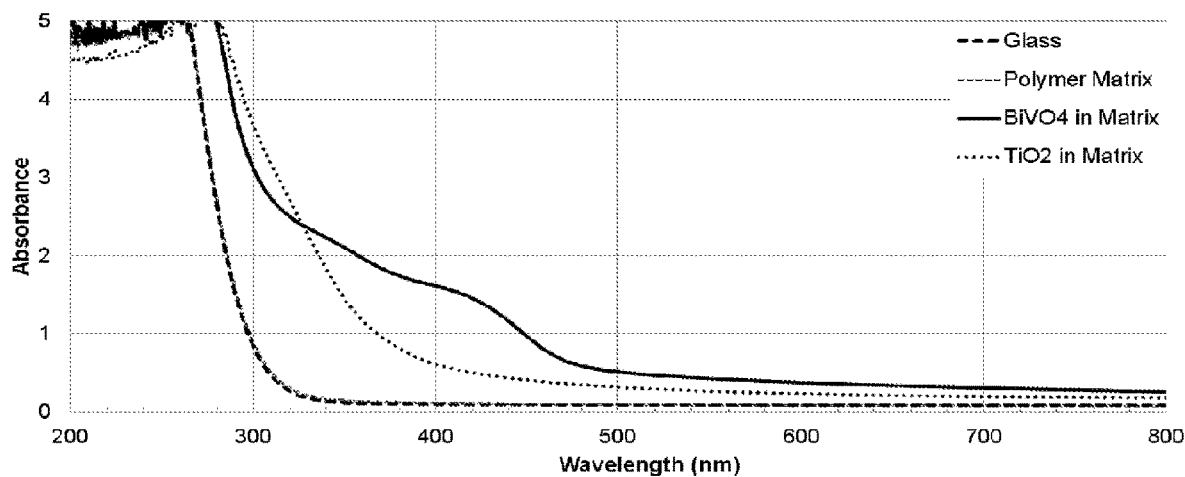
FIG. 4 is a line graph showing absorbance of bismuth vanadate and titanium dioxide nanoparticles incorporated into the swelled polymer matrix macroparticles of the present disclosure, with the polymer matrix alone and support glass slide alone as controls.

As seen in FIG. 4, absorption in the 280-400 nm wavelength range was shown for both titanium dioxide and bismuth vanadate nanoparticles dispersed and embedded in the swelled polymer matrix macroparticles, with no absorbance in this wavelength range for the glass reference or for the swelled polymer matrix macroparticles alone. As an absorbance value of about 1 indicates a UV blocking of at least about 90%, it can be seen that in the present experiment a swelled polymer matrix macroparticle composition comprising nanoparticles of titanium dioxide can effectively block UV radiation up to about 370 nm, whereas a matrix element particle composition comprising nanoparticles of bismuth vanadate can block radiation to about 450 nm, fully covering the UV range. Even at an absorbance value of 2, indicating blocking of up to 99% of the radiation, the swelled polymer matrix macroparticle composition comprising the nanoparticles of bismuth vanadate can block radiation up to about 360 nm, i.e. all of the UVB range and part of the UVA range.

The absorbance patterns of the nanoparticles of the two UV-protective agents herein exemplified, though not identical, are highly similar if measured in the liquid oil media, where such particles are dispersed and freely subject to Brownian motion, or in the film of matrix elements, where such particles are immobilized. Importantly, the substantial lack of red shift in the matrix macroparticles as compared to the oil dispersion indicates that the nanoparticles embedded in the polymer matrix did not agglomerate relatively to their original dispersions. Such aggregation of particles would have caused higher scattering and a shift of the absorbance curves towards higher wavelengths, the extent of which may be undesired for particular applications wherein the compositions should be preferably invisible on the target surface. The present findings support that the nanoparticles are well dispersed within the matrix macroparticles of the compositions according to the disclosure.

Example 7

Scanning Electron Microscope Studies

The bismuth vanadate and titanium dioxide nanoparticles dispersed and embedded in the swelled polymer matrix macroparticles, as prepared in Example 4, were also studied by High Resolution Scanning Electron Microscopy (HR-SEM).

Figure 5:
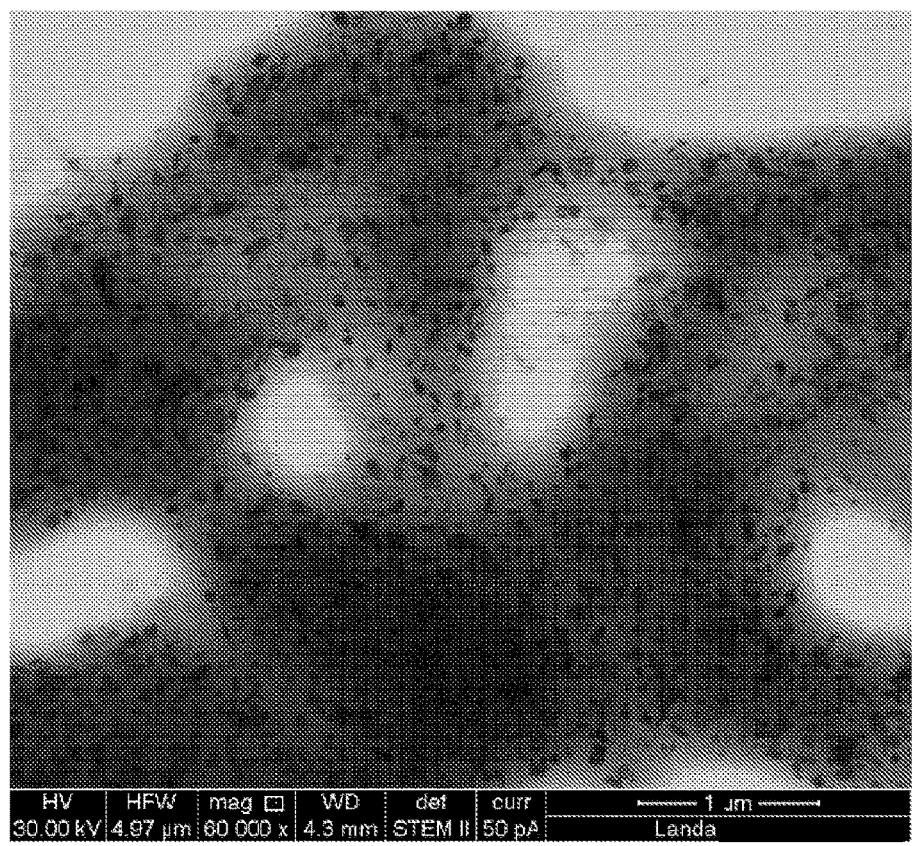
FIG. 5 is a high resolution Scanning Electron Microscope (HR-SEM) image of a portion of a swelled polymer matrix macroparticle, with dispersed titanium dioxide nanoparticles.
Figure 6:
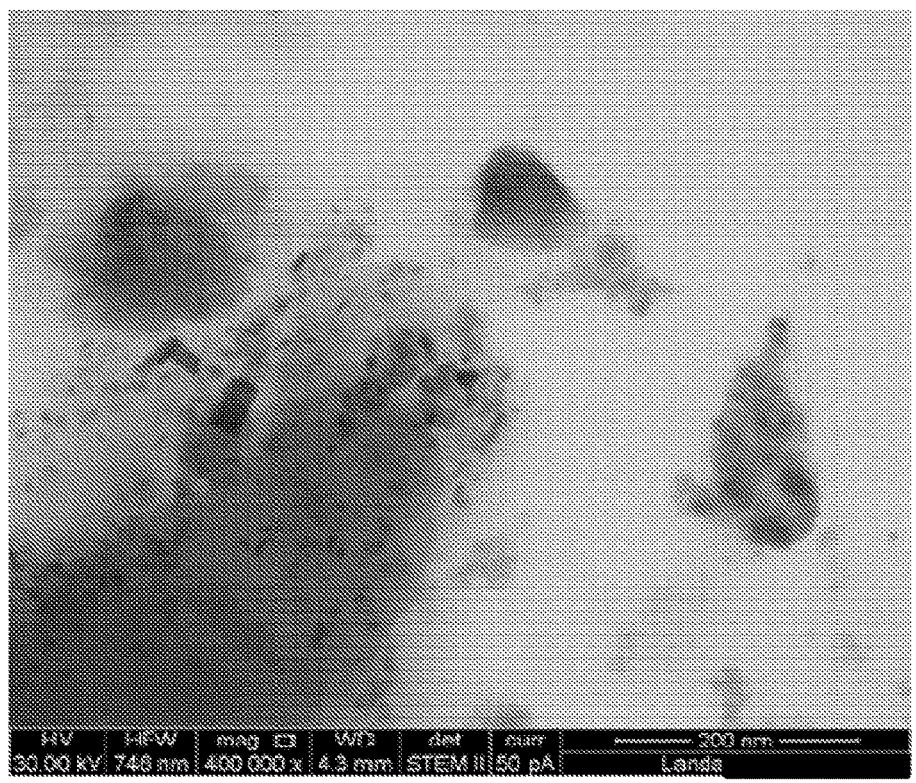
FIG. 6 is a magnified version of the swelled matrix element macroparticles as shown in the HR-SEM image of FIG. 5.

FIGS. 5 and 6 show images for titanium dioxide nanoparticles dispersed and embedded in swelled polymer matrix macroparticles, wherein FIG. 6 is a magnified version of a matrix element as shown in FIG. 5.

Figure 7:
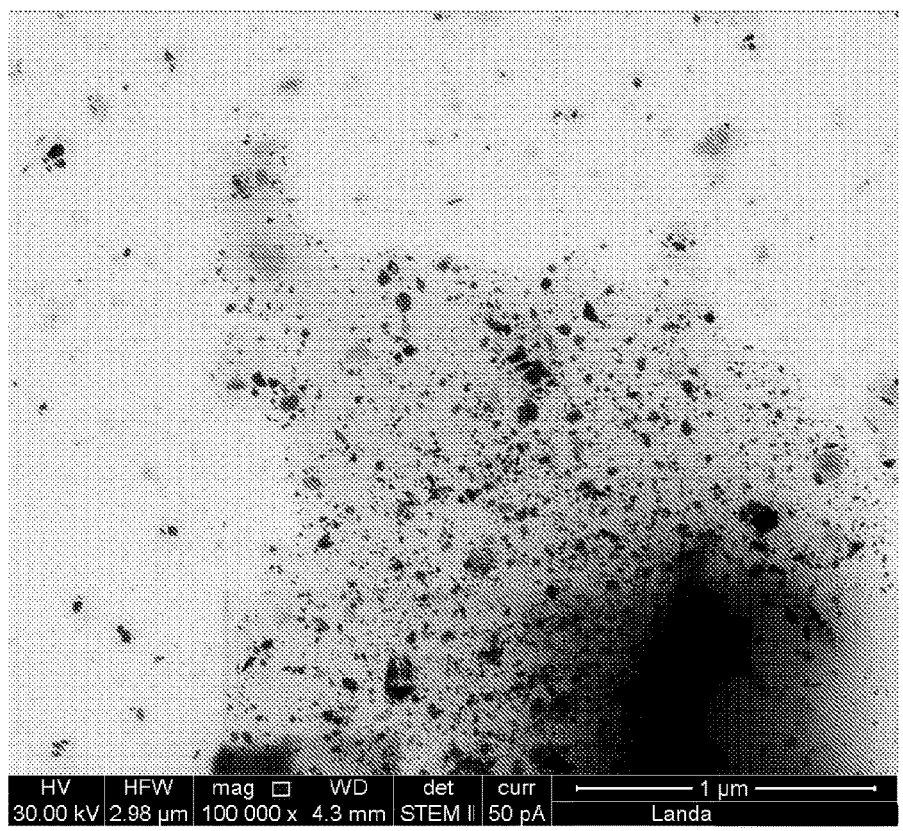
FIG. 7 is a HR-SEM image of a portion of a swelled polymer matrix macroparticle, with dispersed bismuth vanadate nanoparticles.
Figure 8:
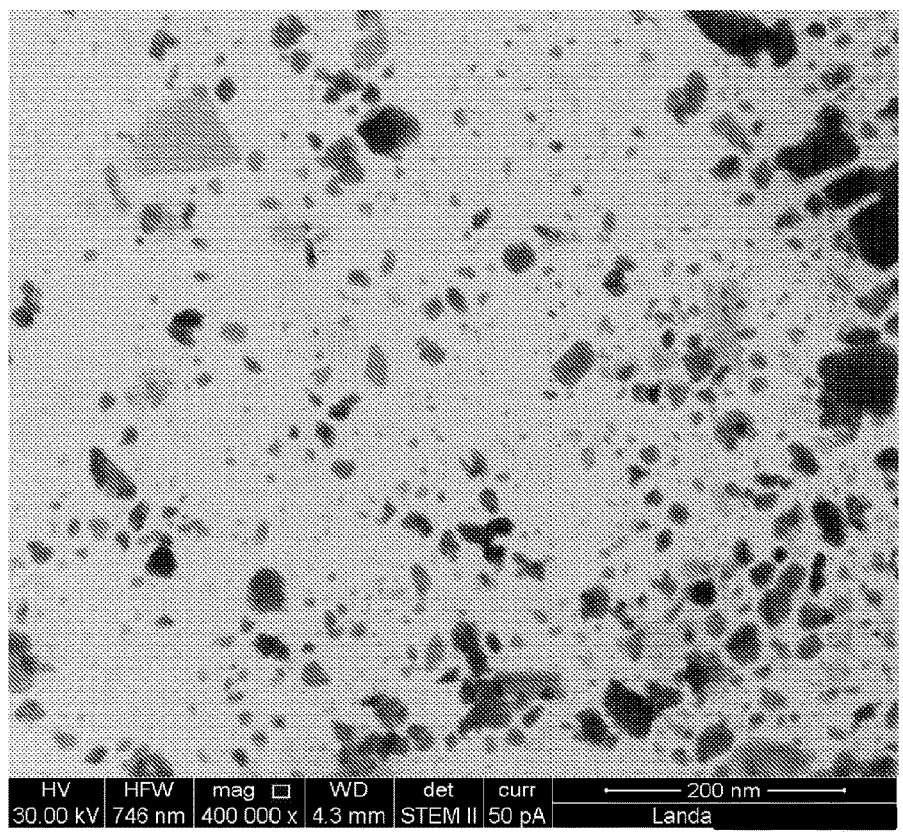
FIG. 8 is a magnified version of the swelled polymer matrix macroparticle as shown in the HR-SEM image of FIG. 7.

FIGS. 7 and 8 show images for bismuth vanadate nanoparticles dispersed and embedded in swelled polymer matrix macroparticles, wherein FIG. 8 is a magnified version of a matrix element as shown in FIG. 7.

As shown in the Figures, nanoparticles having a spheroid shape with diameters of less than about 100 nm, mainly less than about 70 nm, were obtained. The apparent larger clusters are, in reality, not aggregated, and are attributed to the presence of individual, separate nanoparticles disposed at different depths across the matrix element. The good correlation between the diameters of the inorganic nanoparticles when measured in suspension and in dried form confirms the suitability of the above-described method to prepare nanoparticles of inorganic material having a characteristic dimension (e.g. a hydrodynamic diameter) of up to about 100 nm.

Such microscopic field of views may be further analyzed to assess that the nanoparticles are relatively uniformly dispersed. Three cells of view of same size were drawn in FIG. 8, the number of particles in each cell counted, the average number per cell calculated and compared to the measurements of each cell. The number of nanoparticles in the selected cells of view differed from the average of all cells by less than 30%.

Example 8

Determination of Critical Wavelength

Based on the absorbance spectra determined in Examples 5 and 6, critical wavelength was calculated for nanoparticles of TiO$_2$ (D95~94 nm) and BiVO$_4$ (D95~49 nm) either before or after incorporation in the swelled polymer matrix macroparticles.

Briefly, in order to quantify the breadth of UV protection, the absorbance of the sunscreen composition was integrated from 290 nm to 400 nm the sum reached defining 100% of the total absorbance of the UV-protective composition in the UV region. The wavelength at which the summed absorbance reaches 90% absorbance was determined as the 'critical wavelength' which provided a measure of the breadth of UV protection.

The critical wavelength $\lambda_c$ was defined according to the following equation:

$$\int_{290}^{\lambda_c} Ig[1/T(\lambda)]d\lambda = 0.9 \cdot \int_{290}^{400} Ig[1/T(\lambda)]d\lambda$$

wherein:
$\lambda_c$ is the critical wavelength;
$T(\lambda)$ is the mean transmittance for each wavelength; and
$D\lambda$ is the wavelength interval between measurements.

Critical wavelengths as calculated are presented in Table 4 below.

TABLE 4

| Inorganic Material/Step | Critical Wavelength (nm) |
|---|---|
| BiVO$_4$ nanoparticles without swelled polymer matrix macroparticles | 387 |
| BiVO$_4$ nanoparticles dispersed and embedded in swelled polymer matrix macroparticles | 385 |

TABLE 4-continued

| Inorganic Material/Step | Critical Wavelength (nm) |
|---|---|
| TiO$_2$ nanoparticles without swelled polymer matrix macroparticles | 378 |
| TiO$_2$ nanoparticles dispersed and embedded in swelled polymer matrix macroparticles | 371 |

As can be seen from the above table, nanoparticles of inorganic materials dispersed and embedded in swelled polymer matrix macroparticles to form the compositions according to the present teachings allows retention of the UV protective effect of the particles, as expressed by the highly similar critical wavelengths before and after said incorporation.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the disclosure.

The invention claimed is:
1. A UV-protective composition comprising:
   swelled polymer matrix flakes comprising a thermoplastic polymer swelled with an oil; and
   a plurality of nanoparticles including inorganic nanoparticles of at least one inorganic UV-protective agent, each of said inorganic nanoparticles comprising at least one solid inorganic crystal and a dispersant associated with said crystal, wherein said inorganic nanoparticles are dispersed and embedded in said swelled polymer matrix flakes;
   wherein each flake of said swelled polymer matrix flakes has a flake length (Lf), a flake width (Wf), and a flake thickness (Tf), said swelled polymer matrix flakes having a dimensionless flake aspect ratio (Rf) defined by:

$Rf=(Lf \cdot Wf)/(Tf)^2$ wherein, with respect to a representative group containing at least 10 of said swelled polymer matrix flakes, an average Rf is at least 5;
   wherein said inorganic UV-protective agent has a Mohs Hardness Number within a range of 3.5 to 8;
   wherein said plurality of inorganic nanoparticles within said representative group has an average particle size (D$_N$50) of at most 100 nm;
   and wherein said thermoplastic polymer comprises at least one ethylene polymer, ethylene-acrylic acid (EAA) polymer, ethylene-methacrylic acid (EMMA) polymer, or ethyl vinyl acetate (EVA) polymer.
2. The UV-protective composition according to claim 1, wherein at least one of said flake length (Lf) and said flake width (Wf) is at most 50 μm, at most 25 μm, at most 10 μm, or at most 5 μm.
3. The UV-protective composition according claim 2, wherein said flake thickness (Tf) is at most 1000 nm.
4. The UV-protective composition according to claim 1, wherein said flake aspect ratio (Rf) is within a range of 5 to 2000.

5. The UV-protective composition according to claim 1, said inorganic nanoparticles having:
(i) a unimodal particle size distribution; or
(ii) an at least bimodal distribution having a first peak representing a first population of particles having a first average size and at least a second peak representing at least a second population of particles having at least a second average size exceeding said first average size, wherein an area under said first peak exceeds a cumulative area under said at least second peak.

6. The UV-protective composition according to claim 1, wherein said nanoparticles having said $D_N50$ have a particle size distribution (PSD) on a particle number basis, a standard deviation of said PSD being at least one of: at most 60 nm or at most 80%.

7. The UV-protective composition according to claim 1, wherein a concentration of said oil, with respect to said thermoplastic polymer, in the swelled polymer matrix flakes, is: (a) within a first range of 10 to 50% on a weight per weight (w/w) basis, or (b) within a second range of 6 to 65%, on a volume per volume (v/v) basis.

8. The UV-protective composition according to claim 1, wherein said solid inorganic crystal comprises a crystal of a metal oxide.

9. The UV-protective composition according to claim 8, wherein said metal oxide is selected from the group consisting of $BaTiO_3$, $Bi_2O_3$, $BiVO_4$, $TiO_2$, $ZnO$, $ZnTiO_4$, and $Bi_4Ti_3O_{12}$.

10. The UV-protective composition according to claim 8, wherein said metal oxide is doped with a metal cation selected from the group consisting of copper, iron, manganese and lanthanum.

11. The UV-protective composition according to claim 1, wherein, with respect to said representative group of said swelled polymer matrix flakes, said $D_N50$ is at most 90 nm.

12. The UV-protective composition according to claim 1, wherein at least 60% of said plurality of nanoparticles have a cumulative particle size ($D_N60$) of at most 100 nm.

13. The UV-protective composition according to claim 1, wherein a concentration of said inorganic nanoparticles, with respect to said thermoplastic polymer, is at least one of:
(a) within a range of 0.1 to 60% on a weight per weight basis, or
(b) within a range of 0.01 to 20% on a volume per volume basis.

14. The UV-protective composition according to claim 1, wherein a concentration of said inorganic nanoparticles, with respect to the UV-protective composition, is at least one of:
(a) within a range of 0.01 to 40% on a weight per weight basis, or
(b) within a range of 0.01 to 20% on a volume per volume basis.

15. The UV-protective composition according to claim 1, wherein said dispersant has a hydrophilic-lipophilic balance (HLB) value of at most 9.

16. The UV-protective composition according to claim 1, wherein said thermoplastic polymer has at least one of a softening point or a melting point not exceeding 200° C.

17. The UV-protective composition according to claim 16, wherein at least one of said softening point or said melting is at least 60° C.

18. The UV-protective composition according to claim 1, formulated as a coating composition for application to an inanimate surface.

19. A UV-protective composition comprising:
swelled polymer matrix flakes comprising a thermoplastic polymer swelled with an oil; and
a plurality of nanoparticles including inorganic nanoparticles of at least one inorganic UV-protective agent, each of said inorganic nanoparticles comprising at least one solid inorganic crystal and a dispersant associated with said crystal, wherein said inorganic nanoparticles are dispersed and embedded in said swelled polymer matrix flakes;
wherein each flake of said swelled polymer matrix flakes has a flake length (Lf), a flake width (Wf), and a flake thickness (Tf), said swelled polymer matrix flakes having a dimensionless flake aspect ratio (Rf) defined by:

$$Rf=(Lf \cdot Wf)/(Tf)^2$$

wherein, with respect to a representative group containing at least 10 of said swelled polymer matrix flakes, an average Rf is at least 5;
wherein said inorganic UV-protective agent has a Mohs Hardness Number within a range of 3.5 to 8;
wherein said plurality of inorganic nanoparticles within said representative group has an average particle size ($D_N50$) of at most 100 nm;
wherein said thermoplastic polymer comprises at least one ethylene polymer, ethylene-acrylic acid (EAA) polymer, ethylene-methacrylic acid (EMMA) polymer, or ethyl vinyl acetate (EVA) polymer;
wherein said flake thickness (Tf) is at most 1000 nm;
wherein a concentration of said inorganic nanoparticles, with respect to the UV-protective composition, is within a range of 0.01 to 40%, on a weight per weight basis;
wherein said dispersant has a hydrophilic-lipophilic balance (HLB) value of at most 9;
and wherein said thermoplastic polymer has at least one of a softening point or a melting point of at least 60° C. and not exceeding 200° C.

* * * * *